US007452709B2

(12) United States Patent
Kitamoto et al.

(10) Patent No.: US 7,452,709 B2
(45) Date of Patent: Nov. 18, 2008

(54) METHOD OF SCREENING PRION DISEASE INFECTION FACTOR

(75) Inventors: Tetsuyuki Kitamoto, Miyagi (JP); Ichiro Miyoshi, Miyagi (JP); Shirou Mohri, Fukuoka (JP)

(73) Assignee: Japan as represented by president of Tohoku University, Miyagi (JP)

(*) Notice: Subject to any disclaimer, the term of this patent is extended or adjusted under 35 U.S.C. 154(b) by 343 days.

(21) Appl. No.: 10/470,848

(22) PCT Filed: Jan. 31, 2002

(86) PCT No.: PCT/JP02/00803

§ 371 (c)(1), (2), (4) Date: Jul. 31, 2003

(87) PCT Pub. No.: WO02/061418

PCT Pub. Date: Aug. 8, 2002

(65) Prior Publication Data

US 2004/0137421 A1 Jul. 15, 2004

(30) Foreign Application Priority Data

Jan. 31, 2001 (JP) ............................ 2001-024279

(51) Int. Cl.
*C12N 7/00* (2006.01)
*C12N 15/82* (2006.01)

(52) U.S. Cl. ..................................... 435/235.1; 800/21

(58) Field of Classification Search ....................... None
See application file for complete search history.

(56) References Cited

FOREIGN PATENT DOCUMENTS

| | | |
|---|---|---|
| WO | WO 97/04814 | 2/1997 |
| WO | WO 00/71575 A1 | 11/2000 |

OTHER PUBLICATIONS

Wall et al., Transgenic livestock: Progress and prospects for the future. 1996, Theriogenology vol. 45, p. 57-68.*

Mullins et al., Molecular Medicine in Genetically Engineered Animals. 1996, Journal of Clinical Investigation vol. 97, p. 1557-1560.*

Houdebine Production of pharmaceutical proteins from transgenic animals. 1994, Journal of Biotechnology. vol. 34, p. 269-287.*

Ebert et al., A Moloney MLV-Rat Somatotropin fusion gene produces biologically active somatotropin in a transgenic pig. 1988, Molecular Endocrinology, p. 277-283.*

Kappel et al., Regulating gene expression in transgenic animals. 1992. Current Opinion in Biotechnology, vol. 3, p. 548-553.*

Hammer et al., Genetic engineering of mammalian embryos. 1986. J. Animal Science. vol. 63, p. 269-278.*

Strojek and Wagner. The use of transgenic animal techniques for livestock improvement. 1988. Genetic Engineering: Principles and Methods vol. 10, Plenum Press, p. 221-246.*

Kitamoto et al., Abnormal isoform of prion protein accumulates in follicular dendritic cells in mice with Creutzfeldt-Jacob disease. 1991, Journal of Virology, vol. 65, p. 6292-6295.*

Race et al., Journal of Virology, Jan. 2000, vol. 74, p. 828-833.*

T. Muramoto et al., "Accumulation of Abnormal Prion Protein in Mice Infected with Creutzfeldt-Jakob Disease via Intraperitoneal Route: A Sequential Study," *Am. J. Pathology*, 143(5): 1470-79 (1993).

M.E. Bruce et al., "Follicular Dendritic Cells in TSE Pathogenesis," *Immunology Today*, 21(9): 442-446 (2000).

T. Muramoto et al., "Species Barrier Prevents an Abnormal Isoform of Prion Protein from Accumulating in Follicular Dendritic Cells of Mice with Creutzfeldt-Jakob Disease," *J. Virology*, 67(11): 6808-10 (1993).

T. Kitamoto et al., "Humanized Prion Protein Knock-in by Cre-Induced Site-Specific Recombination in the Mouse," *Biomed. Biophys. Res. Comm.*, 222: 742-7 (1996).

T. Muramoto et al., "Species Barrier Prevents an Abnormal Isoform of Prion Protein from Accumulating in Follicular Dendritic Cells of Mice with Creutzfeldt-Jakob Disease," *Journal of Virology*, 67(11): 6808-6810 (1993).

G.C. Telling et al., "Transmission of Creutzfeldt-Jakob Disease from Humans to Transgenic Mice Expressing Chimeric Human-Mouse Prion Protein," *Proc. Natl. Acad. Sci. USA*, 91:9936-9940 (1994).

G.C. Telling et al., "Prion Propagation in Mice Expressing Human and Chimeric PrP Transgenes Implicates the Interaction of Cellular PrP with Another Protein," *Cell*, 83:79-90 (1995).

J. Collinge et al., "Unaltered Susceptibility to BSE in Transgenic Mice Expressing Human Prion Protein," *Nature*, 378:779-783 (1995).

A.F. Hill et al., "The Same Prion Strain Causes vCJD and BSE," *Nature*, 389:448-450 (1997).

E.A. Asante et al., BSE Prions Propagate as Either Variant CJD-like or Sporadic CJD-like Prion Strains in Transgenic Mice Expressing Human Prion Protein, *The EMBO Journal*, 21(23):6358-6366 (2002).

C.I. Lasmézas et al., "Transmission of the BSE Agent to Mice in the Absence of Detectable Abnormal Prion Protein," *Science*, 275:402-404 (1997).

K. Nakamura, "Studies Regarding Technical Developments for Clarification of Mechanism of Abnormal Expression of Brain Functions due to Exogenous Factors (Phase II: years 1995 to 1997), Reports on the Study Results," pp. 221-228 (Mar. 1999). English-language translation attached.

(Continued)

*Primary Examiner*—Stacy B Chen
*Assistant Examiner*—Agnieszka Boesen
(74) *Attorney, Agent, or Firm*—Finnegan, Henderson, Farabow, Garrett & Dunner, L.L.P.

(57) ABSTRACT

Early detection of infectious agents of human prion diseases such as CJD by using an animal model, etc. is needed in order to rapidly determine prion infections in pharmaceuticals such as blood products, foods, or cosmetics. This invention provides a screening method for infectious agents of human or non-human prion diseases in samples, which employs, as an indication, the deposition of the aberrant prion protein in the follicular dendritic cell (FDC) of a non-human animal.

5 Claims, 6 Drawing Sheets
(3 of 6 Drawing Sheet(s) Filed in Color)

OTHER PUBLICATIONS

Mohri, S. et al., "Detection of Prion Accumulation in FDCs of NZW/ Sea and I/LnJ Mice", Annual Report of the Slow Virus Infection Research Committee; The Ministry of Health and Welfare of Japan 1997, Koseisho Tokutei Shikkan Chihatsusei Virus Kansen Chosa Kenkyuhan Heisei 8 nendo (1996) Kenyku Hokokusho Heisei 9 nen, pp. 37-42, (1997).

Nakamura, K. et al., "Humanized Gene Expression in Mice by Using Universal Gene Replacement", Department of DNA Biology and Embryo Engineering, The Institute of Medical Science, The University of Tokyo, and Department of Neurological Science, Tohoku University School of Medicine, Koseisho Tokutei Shikkan Chihatsusei Virus Kansen Chosa Kenkyuhan Heisei 8 nendo (1996) Kenyku Hokokusho Heisei 9 nen, pp. 25-28 (1997).

Extended European Search Report mailed Jun. 3, 2008, for European Patent Application No. 08000541.6 (4 pages).

Telling, "Prion protein genes and prion diseases: studies in transgenic mice," Neuropathology and Applied Neurobiology, 26: 209-220 (2000).

* cited by examiner

Structure of recombinant prion protein a: Infected spleen b: Control spleen c: Infected brain a: Ki-ChM spleen 12.5% b: Ki-ChM spleen 25% c: Ki-ChM spleen 50% d: Ki-ChM spleen 100% e: Tg129#12 spleen 100%

METHOD OF SCREENING PRION DISEASE INFECTION FACTOR

CROSS REFERENCE TO RELATED APPLICATIONS

This application is a National Phase Application based on PCT/JP02/00803, filed Jan. 31, 2002, the content of which is incorporated herein by reference, and claims the priority of Japanese Patent Application No. 2001-024279, filed Jan. 31, 2001.

TECHNICAL FIELD

The present invention relates to a screening method for infectious agents of human or non-human prion diseases in samples, novel recombinant prion proteins, and transgenic animals and knock-in animals that express the aforementioned proteins.

BACKGROUND ART

Creutzfeldt-Jacob Disease (hereinafter abbreviated to "CJD") is an incurable nervous disease which gives rise to presenile dementia. Once a patient develops the disease, the patient enters a vegetative state, a so-called bedridden state, in about 3 to 5 months, and eventually dies. At present, there is no effective therapy for CJD, and only a symptomatic treatment is provided.

CJD is known not only as a neurodegenerative disease that simply develops mental deterioration but also as a disease that is transmitted from human to human or from animal to animal. Examples of human to human transmission are: the kuru disease, which is considered to be transmitted by eating a human brain; CJD transmitted by a growth hormone preparation; and CJD after dura mater transplantation, which has been recently an issue of concern. New variant CJD (nvCJD), which has been an issue of concern in Britain, is considered to arise from the transmission of bovine spongiform encephalopathy (abbreviated to "BSE" and generally referred to as "mad cow disease") from bovine to human.

Based on the assumption that the infectious agent of CJD is made of protein, the infectious agent was designated as a "prion" in 1982. In 1985, the prion protein gene that constitutes the infectious agent, i.e., a prion, was cloned. As a result, it was demonstrated that a prion protein was also expressed in a normal animal brain. Also, the deposition of the aberrant prion protein, which was clearly distinguishable from a normal prion protein, was observed in a patient who had developed the disease. At present, in addition to the aforementioned kuru disease and CJD, Gerstmann-Sträussler Syndrome (abbreviated to "GSS") and fatal familial insomnia (abbreviated to "FFI") are known as so-called prion diseases that result from prion aberrance in humans.

In the case of humans, a prion protein is composed of 253 amino acids (SEQ ID NO: 2), which are bound to the surface of a cell membrane through glycosyl-phosphatidyl-inositol (GPI) after a signal sequence comprising 22 amino acids at the N terminus and 23 amino acids at the C terminus has been removed (SEQ ID NO: 3).

Meanwhile, variations in the prion protein gene was discovered in 1989, and familial GSS or familial CJD was found to develop with the variation of only one amino acid of the prion protein. The prion protein was found to play an important role in CJD.

The aforementioned nvCJD was reported to develop early in people's lives (in their teens to 30's), and the deposition of the aberrant prion protein is observed not only in the central nervous system, which is known in other forms of CJD, but also in the follicular dendritic cell (FDC) in the lymphoid tissue, which was not observed in other forms of CJD (Hill A. F. et al., Lancet 1997, 349: 99-100). It is not known approximately how many nvCJD carriers exist, and this is a serious issue of concern in Britain to such an extent that it is prohibited to supply blood products prepared from domestic blood.

For one of the reasons, the transmission (infection) of prions within the same species is easy, highly transmissible, and short in the incubation period while the transmission across species requires a long incubation period and is low rate of transmission. Because of this across-species barrier, it was very difficult to detect infectious agents of human prion diseases such as CJD with using an animal model or the like.

For example, an experiment regarding the transmission of the nvCJD to human type transgenic mice has been attempted (Hill, A. F. et al., Nature 1997 , Oct. 2; 389 (6650): 448-50). However, it required a long incubation period (228 days or longer) to develop any symptoms and was not very successful (successful for only 25 out of 56 mice). It has been recently reported that the nvCJD was transmitted in an incubation period of approximately 250 days with the use of bovine-type transgenic mice (Scott M. R. et al., Proc. Natl. Acad. Sci. USA 1999, 96: 15137-42).

A system using transgenic animals has been reported as a method for detecting prions in a sample (JP Patent Publication (Kohyo) No. 11-510496 A (1999)). In an example using mice, the development of scrapie within approximately 50 days has been reported, however, it took approximately 200 days to develop into a human prion disease.

We demonstrated that an aberrant prion protein was deposited in a synapse in the central nervous system of a CJD patient and a CJD-infected mouse using a novel immunostaining procedure that is referred to as the autoclave method (Kitamoto, T. et al., Am. J. Pathol. 140: 1285-1294 (1992); Muramoto, T. et al., Am. J. Pathol. 140: 1411-1420 (1992)). We also found that an aberrant prion protein was deposited in a cell other than one of the central nervous system, i.e., the FDC (Kitamoto, T. et al., J. Virol. 65: 6292-6295 (1991)). The deposition of the aberrant prion protein in the FDC can be detected well before a mouse develops the disease, and thus, a premorbid diagnosis can be performed (Muramoto, T. et al., Am. J. Pathol. 140: 1411-1420 (1992); Muramoto, T. et al., Am. J. Pathol. 143: 1470-1479 (1993)).

Upon the intracranial administration of an infectious agent (mouse prion) to mice, they generally develop the disease in 120 to 140 days. When the deposition of the aberrant prion protein in the FDC is employed as an indication, detection of the infectious agent can be carried out in all the mice after 30 days post administration.

As described above, rapid determination of the prion infection in pharmaceuticals such as blood products requires early detection of infectious agents of human prion diseases such as CJD with using an animal model, or the like.

The deposition of the aberrant prion protein in the FDC was verified only in mice, and it could not be previously detected in human CJD. Due to a species difference between humans and mice, it was known that the deposition of the aberrant prion protein in the FDC was not observed in wild-type mice in the first inoculation for infection from human CJD (Muramoto, T. et al., J. Virol. 67: 6808-6810 (1993)).

Accordingly, a method for directly detecting the aberrance in a human prion protein has been awaited.

DISCLOSURE OF THE INVENTION

Under the above circumstances, we have conducted concentrated studies in which we prepared novel recombinant prion proteins derived from human and mouse prion proteins and prepared transgenic animals and knock-in animals comprising the aforementioned proteins introduced therein. As a result, we succeeded in developing a very effective screening method which can detect infectious agents of human or non-human prion diseases in samples within an unprecedentedly short period of time.

Specifically, the present invention provides the following (1) to (26).

(1) A screening method for infectious agents of human or non-human prion diseases in a sample, which employs, as an indication, the deposition of an aberrant prion protein in the follicular dendritic cell (FDC) of a non-human animal.

(2) The screening method for according to (1) above, wherein the non-human animal is a transgenic animal that expresses a humanized prion protein gene.

(3) The screening method for according to (1) above, wherein the non-human animal is a knock-in animal that expresses a humanized prion protein gene.

(4) The screening method for according to any one of (1) to (3) above, wherein the sample is administered intraperitoneally, intracerebrally, intravascularly, or orally to the non-human animal.

(5) The screening method for according to any one of (1) to (4) above, wherein the deposition of the aberrant prion protein in the FDC is detected by a histological detection method, electrophoresis, and/or binding assay.

(6) The screening method for according to any one of (1) to (5) above, wherein the deposition of the aberrant prion protein in the FDC is detected 14 to 700 days after the sample administration.

(7) The screening method for according to any one of (1) to (6) above, wherein the humanized prion protein is prepared by substituting a part of the exon 3 of the non-human animal prion protein gene with a part of the exon 3 of the human prion protein.

(8) The screening method for according to any one of (1) to (6) above, wherein the humanized prion protein is prepared by substituting 6 residues on the C-terminal side among human-specific amino acid residues in the human prion protein with corresponding amino acid residues in the non-human animal prion protein that is used in the screening.

(9) The screening method for according to any one of (1) to (6) above, wherein the humanized prion protein comprises an amino acid sequence as shown in SEQ ID NO: 6 or 7.

(10) A recombinant humanized prion protein, which is encoded by a recombinant gene in which a part of the exon 3 of the non-human animal prion protein gene is substituted with a part of the exon 3 of the human prion protein gene.

(11) A recombinant humanized prion protein, wherein 6 residues on the C-terminal side among human-specific amino acid residues in the human prion protein are substituted with corresponding amino acids in non-human animal prion protein.

(12) A recombinant humanized prion protein, which comprises an amino acid sequence as shown in SEQ ID NO: 6 or 7.

(13) A gene or a fragment thereof, which encodes the protein according to any one of (10) to (12) above.

(14) A gene or a fragment thereof, which comprises a nucleotide sequence as described in the following:

(a) the nucleotide sequence as shown in SEQ ID NO: 4;

(b) a nucleotide sequence that is a degenerate sequence of the nucleotide sequence as shown in SEQ ID NO: 4; or (c) a nucleotide sequence that is hybridizable with the sequence according to (a) or (b) under stringent conditions and encodes the protein according to (10) above.

(15) A vector, which comprises the gene or a fragment thereof according to (13) or (14) above.

(16) A transgenic animal having the gene or a fragment thereof according to (13) or (14) above introduced therein.

(17) A knock-in animal having the gene or a fragment thereof according to (13) or (14) above introduced therein.

(18) A transgenic animal, which expresses a humanized prion protein in the FDC.

(19) A knock-in animal, which expresses a humanized prion protein in the FDC.

(20) A transgenic animal, which expresses the protein according to any one of (10) to (12) above in its brain and/or FDC.

(21) A knock-in animal, which expresses the protein according to any one of (10) to (12) above in its brain and/or FDC.

(22) A method for producing a transgenic animal, which expresses the protein according to any one of (10) to (12) above.

(23) A method for producing a knock-in animal, which expresses the protein according to any one of (10) to (12) above.

(24) The method for producing a knock-in animal according to (23) above comprising the following steps of:

(a) constructing a vector containing a non-human prion protein gene or a fragment thereof;

(b) substituting a part of the exon 3 of the non-human prion protein gene with a part of the exon 3 of a human prion protein;

(c) inserting a loxp-surrounded antibiotic-resistant gene into the 3'-non-translation region;

(d) introducing the resulting modified vector into the non-human ES cell;

(e) producing a chimera animal from a clone having homologous recombination; and (f) removing the antibiotic-resistant gene by introducing a Cre enzyme-expressing plasmid into a fertilized egg of the F1 animal.

(25) A screening method for a preventive and/or therapeutic agent for human or non-human prion diseases, which utilizes the transgenic animal according to (18) or (20) above or the knock-in animal according to (19) or (21) above.

(26) A method, which utilizes the transgenic animal according to (18) or (20) above or the knock-in animal according to (19) or (21) above, for performing safety tests on various pharmaceuticals such as blood products derived from human or non-human animal organs, foods, or cosmetics.

This description includes part or all of the content as disclosed in the description and/or drawings of Japanese Patent Application No. 2001-24279, which is a priority document of the present application.

BRIEF DESCRIPTION OF DRAWINGS

The patent or application file contains at least one drawing executed in color. Copies of this patent or patent application publication with drawings will be provided by the Office upon request and payment of the necessary fee.

DESCRIPTION OF SEQUENCE LISTINGS

Figure 1:
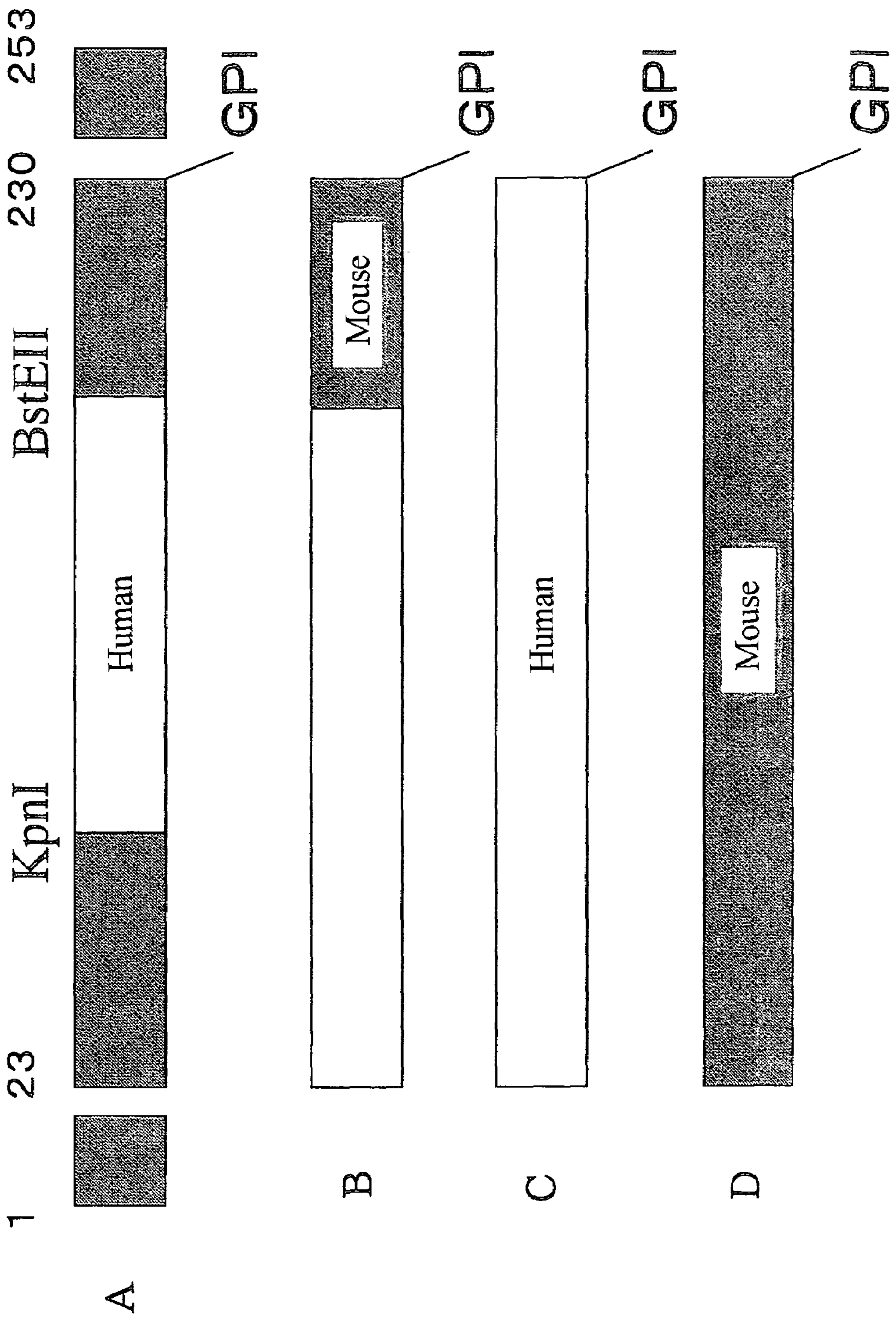
FIG. 1 is a diagram schematically showing the structure of the recombinant prion protein according to the present invention.

SEQ ID NO: 4 shows a nucleotide sequence of a chimeric prion gene.

SEQ ID NO: 5 shows an amino acid sequence of a chimeric prion protein.

SEQ ID NO: 6 shows an amino acid sequence of a ChM-type prion protein.

SEQ ID NO: 7 shows an amino acid sequence of a ChV-type prion protein.

EMBODIMENTS FOR CARRYING OUT THE INVENTION

The present invention is hereafter described in more detail.

In this description, the term "non-human animal" refers to: a mammalian animal such as a mouse, rat, hamster, guinea pig, rabbit, pig, cattle, sheep, cat, or dog; bird; or fish. In the present invention, non-human animals are not particularly limited, and a mouse is particularly preferable from the viewpoints of breeding and handling.

In this description, the term "aberrant prion protein" refers to a prion protein, which has a conformation that is different from that of a normal prion protein, is made insoluble by a surfactant, and is not partially digested with protease. In human and animal prion diseases, this aberrant prion protein is always present in addition to a normal prion protein. This presence can be confirmed by, for example, Western blotting after treatment with protease, detection of amyloid fibers constituted by an aberrant prion protein using an electron microscope after the extraction of the protein, or detection by immunostaining utilizing the autoclave method, which we have developed (Shin, R. W. et al., Lab. Invest. 64: 693-702 (1991); Kitamoto, T. et al., J. Virol. 65: 6292-6295 (1991); Kitamoto, T. et al., Am, J. Pathol. 140: 1285-1294 (1992)).

The term "infectious agent" used herein refers to a factor that is capable of developing the prion disease when administered to a human or the transgenic animal or knock-in animal according to the present invention. Specific examples thereof include an aberrant prion protein derived from human or non-human animals or a fragment thereof, and a substance comprising the same. Examples of such samples comprising infectious agents include pharmaceuticals such as blood products derived from human or non-human animals, foods, and cosmetics.

Further, the term "humanized prion protein" used herein refers to a prion protein in which a part thereof, which is originally expressed by its non-human animal host, is substituted with a sequence of a human prion protein. Examples thereof include a recombinant humanized prion protein that is encoded by a recombinant gene in which a part of the encoding region in a non-human animal prion protein gene has been substituted with a corresponding region of a human prion protein gene, and a recombinant humanized prion protein in which a part of the residues in the human-specific amino acid residues of the human prion protein has been substituted with corresponding amino acid residues of the non-human animal prion protein.

An example of a humanized prion protein that is particularly preferably used in the present invention is a recombinant humanized prion protein, which is encoded by a recombinant gene in which a part of the exon 3 in the non-human animal prion protein gene is substituted with a part of the exon 3 in the human prion protein gene. This recombinant humanized prion protein can be obtained in the following manner. A part of the exon 3 in the prion protein gene of the non-human animal such as a mouse is substituted with a part of the exon 3 in the human prion protein gene by recombination to obtain a gene, and the resulting gene is incorporated into, for example, a vector to introduce it into a host to be expressed therein. The phrase "a part of the exon 3" refers to a sequence that essentially comprises the region between the SmaI site and the BstEII site in the prion protein translation region of the exon 3. In the prion protein gene, a protein translation region is present only in the exon 3.

Techniques of genetic engineering that are described in this description such as gene recombination are commonly used in the art, and those skilled in the art can suitably carry out them based on the description given herein.

Specifically, the humanized prion protein according to the present invention is expressed by a knock-in animal that is obtained by, for example, the following steps of:

(a) constructing a vector containing a non-human prion protein gene or a fragment thereof;

(b) substituting a part of the exon 3 of the non-human prion protein gene with a part of the exon 3 of a human prion protein;

(c) inserting a loxp-surrounded antibiotic-resistant gene into the 3'-non-translation region;

(d) introducing the resulting modified vector into the non-human ES cell;

(e) producing a chimera animal from a clone having homologous recombination; and (f) removing the antibiotic-resistant gene by introducing a Cre enzyme-expressing plasmid into a fertilized egg of the F1 animal.

The humanized prion protein can be obtained by any technique known to those skilled in the art such as site-directed mutagenesis or chemical synthesis as one in which, among amino acid residues that are known to be human-specific, for example, 6 residues on the C-terminal side of the human prion protein are substituted with corresponding amino acid residues of the non-human animal prion protein.

The base sequence of the human prion protein gene is known to be the one as shown in SEQ ID NO: 1 and the amino acid sequence thereof is known to be the total amino acid sequence as shown in SEQ ID NO: 2. It becomes a mature protein through processing with a signal sequence comprising 22 amino acids at the N-terminus and an amino acid sequence as shown in SEQ ID NO: 3 from which 23 amino acids at the C-terminus have been deleted. In SEQ ID NO: 3, residues 33, 34, 50, 58, 75, 87, 90, 116, 121, 123, 133, 144, 146, 193, 197, 198, 205, 206, and 208 are presumed to be human-specific (Kretzschmar, H. A. et al., DNA 1986, 5: 315-24). We have made various studies concerning the substitution of these human-specific amino acids with corresponding amino acids of non-human animals. As a result, we found that a sequence in which 6 residues on the C-terminal side are substituted with corresponding amino acid residues of the non-human animal prion protein is particularly preferably used in the screening method according to the present invention. An embodiment of this sequence is shown in SEQ ID NO: 6 or 7. SEQ ID NO: 6 is methionine at codon 129, and SEQ ID NO: 7 is valine at codon 129. This polymorphism is observed in a normal human prion protein and is also present in aberrant prion proteins that are observed in various human prion diseases.

The present invention also provides a gene or a fragment thereof encoding the humanized prion protein according to the present invention and a vector comprising the gene or a fragment thereof.

The gene encoding the humanized prion protein according to the present invention encodes a recombinant humanized prion protein comprising an amino acid sequence as shown in SEQ ID NO: 6 or 7. Examples of other forms include a gene comprising a nucleotide sequence as shown in SEQ ID NO: 4, a gene comprising a nucleotide sequence that is a degenerate sequence of the nucleotide sequence as shown in SEQ ID NO: 4, and a gene comprising a nucleotide sequence that is hybridizable with these sequences under stringent conditions. The stringent conditions used herein refer to a set of conditions under which a so-called specific hybrid is formed. For example, nucleotide sequences that are highly complementary to each other, i.e., nucleotide sequences that are at least 90%, and preferably at least 95% complementary to each other hybridize with each other, but nucleotide sequences that are less complementary do not hybridize under these conditions. More specifically, sodium concentration is 15 to 300 mM and preferably 15 to 75 mM, and temperature is between 50 and 60° C. and preferably between 55 and 60° C. A gene may be either DNA or RNA, and it may be obtained by synthesis. A "fragment" refers to a part of the prion protein gene and preferably comprises a nucleotide sequence that encodes the region between codon 85 and codon 230 of SEQ ID NO: 2. Alternatively, a fragment may be a defective type of this sequence, which refers to a sequence comprising at least approximately 300 nucleotides.

Any vector comprising the gene or a fragment thereof may be used as long as the gene can be expressed in a host animal cell into which it has been introduced. The vector is not particularly limited as long as it is used in the art. An example thereof is a vector the expression of which can be observed in any cell, which utilizes an actin promoter. A promoter, enhancer, other regulator gene, or the like that can regulate the expression of the gene can be suitably incorporated. Examples of promoters that can be preferably used in the present invention include a promoter that accelerates the expression in the FDC, such as a promoter of the CD21 (Cr2) gene. A reference can be made to literature, for example, Zabel, M. D. et al., J. Immunol. 2000 Oct. 15; 165 (8): 4437-45.

Meanwhile, the preparation of transgenic mice comprising a prion protein gene introduced therein has been already reported (Telling G. C. et al., Cell 1995, Oct. 6: 83 (1) 79-90). One example is a transgenic mouse, which comprises a completely human-type prion protein gene introduced therein as shown in FIG. 1C. The incubation period therein before the development of CJD was approximately 250 days. Another example is a transgenic mouse, which comprises a protein gene in which the region between the KpnI site and the BstEII site is a sequence derived from a human prion protein, and the N-terminus and the C-terminus are sequences derived from mouse prion proteins introduced therein as shown in FIG. 1A. The incubation period therein is approximately 200 days. In contrast, the transgenic mouse according to the present invention comprises a protein gene in which the region between the N-terminus and the BstEII site is a sequence derived from a human prion protein and the C-terminus is a sequence derived from a mouse prion protein introduced therein as shown in FIG. 1B.

We prepared transgenic mice that comprise a gene (SEQ ID NO: 6 or 7) encoding a protein that is schematically shown in FIG. 1B introduced therein, and succeeded in obtaining mice, the incubation period therein before the development of diseases is 147 days on average in the case of homozygous mice.

Accordingly, the present invention provides transgenic animals that express a recombinant humanized prion protein as shown in SEQ ID NO: 6 or 7. In the present invention, transgenic animals may be homozygous or heterozygous, and homozygous animals are more preferable.

However, it is unknown into which position and chromosome of the transgenic animal the gene is incorporated. In order to obtain a transgenic animal having a short incubation period as described above, it has to be mated with a knockout animal of a prion protein gene. We have previously established a method for substituting genes using the ES cell in which a mouse gene is substituted with a human type gene (Kitamoto, T. et al., Biochem. Biophys. Res. Commun. 222: 742-747 (1996)). We improved this method and prepared knock-in mice in which a part of naturally occurring mouse gene was substituted with a human gene having a sequence as shown in SEQ ID NO: 1. These knock-in mice had the incubation period of 151 days on average.

Specifically, the present invention provides knock-in animals that express the recombinant humanized prion protein as shown in SEQ ID NO: 6, 7, or 10. In the present invention, the knock-in animals may be homozygous or heterozygous, and homozygous animals are more preferable. The expression of recombinant humanized prion proteins are observed in their whole bodies, and the expression can be detected particularly in their brains and/or spleens.

An advantage of the method for substituting genes using the ES cell is that it eliminates the need for mating with a knockout animal to remove a mouse endogenous prion protein, which was problematic in the case of the transgenic animals. Also, the distribution and the level of gene expression are similar to those of normal animals, and thus, completely natural expression can be realized.

When human or non-human animal-derived infectious agents are administered to the model animals comprising humanized prion proteins introduced therein, it is presumed that the deposition of the aberrant prion protein is detected in the FDC. Accordingly, human-type transgenic animals can be used for a method for rapidly screening infectious agents that employs the deposition of the aberrant prion protein in the FDC as an indication.

Figure 2A:
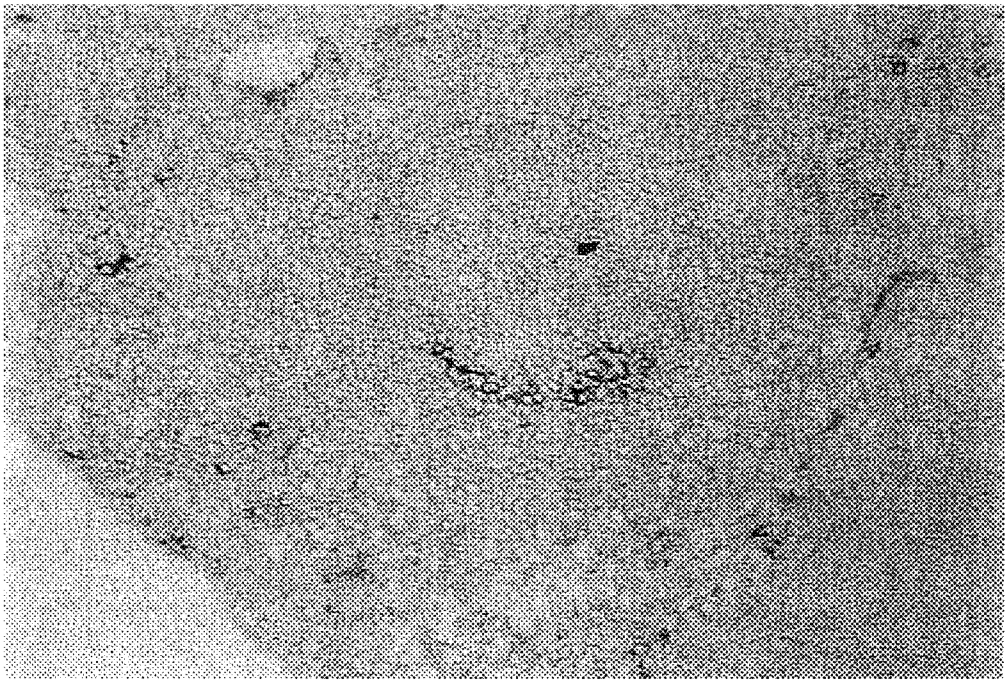
FIG. 2A shows the deposition of the aberrant prion protein in the FDC.

Based on the above presumption, we investigated the FDC after the resulting transgenic and knock-in mice developed the disease. Accordingly, aberrant prion proteins were not substantially detected in the transgenic mice, however, the human-type aberrant prion proteins were found to be deposited in the FDC of the spleen, lymph node, and intestinal lymphoid tissue (Peyer's patch) of the knock-in mice (FIG. 2A).

Figure 2B:
FIG. 2B shows immunostaining using an antibody that recognizes the C-terminus of a human-type prion protein.

Up to the present, it was impossible to determine whether the deposition of the aberrant prion proteins in the FDC was caused by aggregation of aberrant prion proteins contained in the materials that were administered at the time of infection experiment or caused by conversion of normal prion proteins into aberrant prion proteins in the FDC. The C-terminus of the recombinant prion protein as shown in SEQ ID NO: 6 or 7 according to the present invention is of a mouse-type as described above. Accordingly, we then prepared an antibody to the C-terminus of the human-type prion protein. The FDC was investigated using this antibody, and the FDC could not be stained (FIG. 2B). This indicates that the aberrant prion proteins deposited in the FDC were not simple aggregation of human-type aberrant prion proteins contained in the infectious agents.

Figure 3:
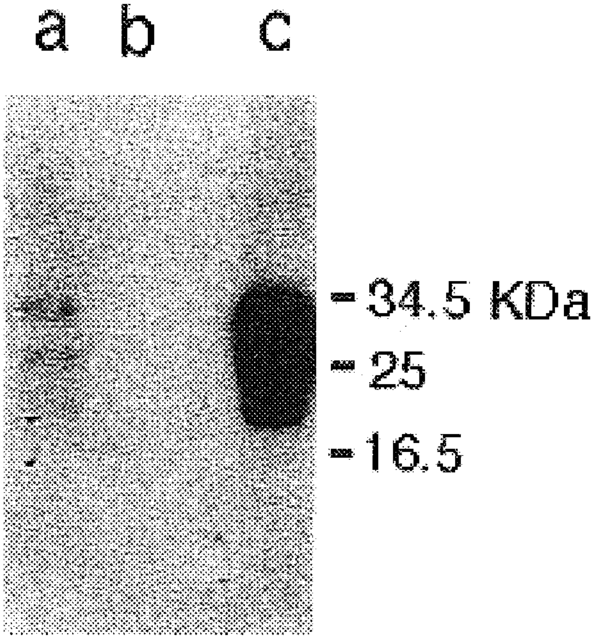
FIG. 3 shows, by Western blotting, an infection with an aberrant prion protein in the spleen and in the brain.

We further examined the deposition of the aberrant prion proteins in the spleen by Western blotting, which was already confirmed by immunostaining. We confirmed the presence of the aberrant prion protein in the spleen of the knock-in mouse (FIG. 3). Furthermore, the infectivity in the spleen was confirmed by the direct infection experiment.(Table 2, Inoculation Experiment 3).

The knock-in mice that we prepared had an incubation period of 151 days on average before the development of the disease. We examined the shortest period before the deposition of the aberrant prion proteins in the FDC could be detected. As a result, it was found out that detection could be made in a very short time period of 14 days in the assay system using the knock-in mice according to the present invention (Table 6).

In contrast, the Ki-HuM mice that expressed complete human prion proteins (8 amino acids are deleted from SEQ ID NO: 10) required a very long incubation period of 643 days, although all of them developed the disease. In the immunohistostaining of the FDC in the spleen 75 days after the intraperitoneal inoculation, the rate of detection was jut 80% (4 out of 5 mice). As with the case of Ki-ChM, the deposition of the aberrant prion protein in the FDC was confirmed (Table 7). Specifically, with the use of the knock-in method in which the prion protein is effectively expressed in the FDC, aberration of prion protein was effectively observed in the FDC in the completely human-type animal to some extent. In this type of animal, the aberration of the prion protein is less likely to occur in the brain. Accordingly, with the use of the knock-in animals prepared by the method, which we claimed wherein the prion protein is effectively expressed in the FDC, it is possible to detect the deposition of the aberrant prion protein of non-human animals such as cattle in the FDC of the knock-in mouse, which expresses the prion protein of non-human animals such as cattle, as well as the prion protein gene in which a specific region in the knock-in animal has been substituted.

The knock-in animal according to the present invention was found to be unprecedentedly highly susceptible to prions as described above. Accordingly, the present invention also provides a biological assay, which employs the knock-in animal according to the present invention, and the deposition of the aberrant prion protein in the FDC thereof as an indication, thereby detecting the development of the human or non-human animal prion diseases in any given samples. This assay can be used as a screening method for the infectious agents of the prion diseases in any given samples.

Examples of samples include various pharmaceuticals such as blood or blood products derived from human or non-human animal organs, foods, and cosmetics. The sample is allowed to infect non-human animals, preferably transgenic animals that express humanized prion proteins, and particularly preferably the knock-in animals according to the present invention. The sample may be administered intraperitoneally, intracerebrally, intravascularly, or orally. Intraperitoneal administration is preferable since a relatively large amount of sample can be administered as described below. More specifically, for example, approximately 2 ml of a solution containing blood, organ, or a preparation derived therefrom is administered to the knock-in animals intraperitoneally to infect them.

After the infection, the deposition of the aberrant prion protein in the FDC can be detected to determine whether the prion disease was developed or not using the sample. Any detection method may be used as long as it can detect the deposition of the aberrant prion protein in the FDC. Examples of detection methods include histological detection in which the deposition of the aberrant prion protein in the FDC of the Peyer's patch, which is a lymphoid tissue of the spleen, lymph node, or intestine is observed using an electron microscope, etc., electrophoresis, and/or in situ hybridization, Western blotting, or ELISA in which the antibody to the aberrant prion protein is labeled with a radioactive or nonradioactive label and binding assay is conducted. Detection may be carried out with the elapse of time after the infection. Alternatively, the period before the aberrant prion protein is deposited in the FDC in the presence of the infectious agents is previously determined by the control sample, and the deposition of the aberrant prion protein in the FDC may be detected after a determined period has elapsed following sample infection, for example, 75 days. The period of detection is not particularly limited as long as it is between 14 days and 700 days after the administration. The deposition of the aberrant prion protein in the FDC can be employed as an indication to determine the presence of the infectious agent within a significantly shorter period of time than conventional methods.

Up to the present, no cases at all were reported in which the aberrant prion protein has been observed in the FDC of a mouse model of human prion diseases, especially CJD. This is consistent with the fact that CJD is substantially sporadic and is not caused by exogenous infection. nvCJD, which occurred in Britain in 1996, is considered to be associated with the infectious agents derived from bovine spongiform encephalopathy and is classified as a transmissible prion disease. Accordingly, it is very critical to be able to detect the infectious agent.

The present invention also provides a screening method wherein the infectious agent is administered intraperitoneally, intracerebrally, intravascularly, or orally.

In the past, the infection experiments were mainly carried out by intracerebral administration. When a sample containing the infectious agent is administered intracerebrally, the dose is limited. The sample can be administered to the brain of a mouse only in an amount of 20 μl at the maximum, however, 2 ml of the sample can be administered to the abdominal cavity. In addition, the administration can be made several times.

In a biological assay for general organs comprising blood in which the concentration of the infectious agents are considered to be low, this quantitative difference of as much as 100 times is significant and affects the detection sensitivity. In the case of mice infected with CJD, for example, LD50 is $10^{-8}$/g in the brain and $10^{-3}$/g or lower in the blood according to infection experiments by intracerebral administration. These results were obtained when 20 μl of the sample was used for intracerebral administration. In contrast, when 100-fold amount of the sample were intraperitoneally administered, the concentration in the organ (blood) having LD50 of $10^{-3}$/g was brought to the same level as highly sensitive organs (such as the spleen) having LD50 corresponding to $10^{-5}$/g. Accordingly, intraperitoneal administration is a method with much promise as a future screening method for the infectious agents in samples.

Up to the present, no report has been made concerning the development of the disease upon intraperitoneal administration of the infectious agents to a human-type transgenic mouse model. The data on the transgenic mouse that we presented suggests the difficulty of developing the disease from the periphery by intraperitoneal administration without the deposition of the aberrant prion protein in the FDC. In the SCID (deficient of T cell and B cell) mouse, which developed the disease by intracranial administration but does not develop the disease by intraperitoneal administration, the deposition of the aberrant prion protein in the FDC is not observed. This indicates that the aberrant prion protein is not transmitted to the brain without the deposition thereof in the FDC.

In the knock-in mice according to the present invention, the human-type aberrant prion protein was deposited only after the administration of the infectious agents. They were subjected to intraperitoneal administration. After an average of 283 days following the administration, all 11 mice had developed the diseases. Specifically, the infection of a human prion through the periphery was successfully performed for the first time in the present invention (Table 5).

Further, the present invention provides a screening method for preventive and/or therapeutic agents for human or non-human prion diseases, which utilizes the transgenic animal of the present invention or the knock-in animal of the present invention.

As described above, the deposition of the aberrant prion protein in the FDC can be detected within a short period after administration of infectious agent at high sensitivity with the use of the transgenic animal or knock-in animal according to the present invention. Screening can be performed with this technique in which an agent, which is capable of blocking the deposition of the aberrant prion protein in the FDC or the migration thereof from the FDC to the brain, can be administered to test animals before and after the administration of the infectious agent or simultaneously with the administration of the infectious agent. This enables the development of preventive and/or therapeutic agents for human or non-human prion diseases, which has been and is currently seriously problematic and any effective agent for which has not yet been reported.

Prion diseases that are observed in various animals can be assayed using a knock-in mouse comprising the prion protein gene of the animal of interest incorporated therein.

EXAMPLE

Example 1

Preparation of Knock-in Vector

Figure 4:
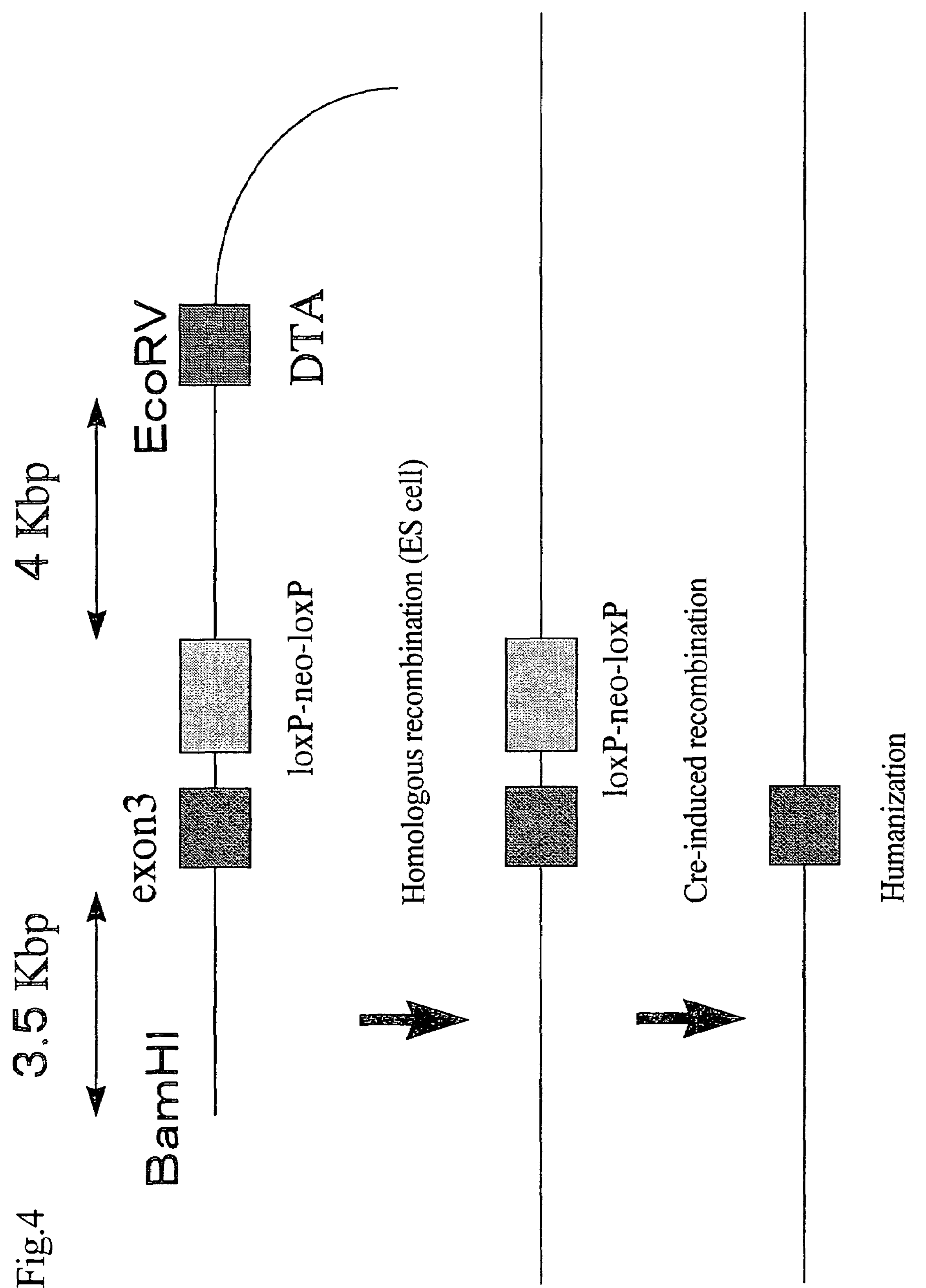
FIG. 4 shows an embodiment of humanization by a vector used in the preparation of the knock-in animals according to the present invention (knock-in vector), homologous recombination, or Cre-induced recombination.

In order to prepare a recombinant human prion protein, an approximately 10 kbp construct was selected as a vector for gene substitution. This construct was centered on the exon 3 in which the region between glycine (amino acid 40, nucleotide 118) and threonine (amino acid 187, nucleotide 561) in the translation region of the exon 3 of the mouse prion protein gene (SEQ ID NO: 8 and SEQ ID NO: 9: amino acid sequences) was substituted with a human prion protein gene. As a knock-in vector, a 3.5 kbp region between the BamHI site of the intron 2 and the SmaI site of the exon 3 of the mouse prion protein gene having an intron as long as 20 kbp was used, the region between the SmaI site and the BstEII site of the exon 3 was substituted with a human prion protein gene, and the loxp-surrounded PGK-neo gene was inserted into the ApaI site, which is a 3'-non-translation region of the exon 3 (FIG. 4). A mouse gene was used for the 3' region, which was as large as 4 kbp between ApaI and EcoRV.

As a negative selection, the diphtheria toxin DTA gene was inserted into the 3' side, and a plasmid was linearized with NotI and then introduced into the ES cell by electroporation. The ES cell was analyzed by Southern blotting by selecting 120 clones after G418 selection (neomycin selection). Homologous recombination was observed in 4 out of 120 analyzed clones. This was more effective compared to our previous experiment using loxP-neo-gpt-loxP in which a positive clone was obtained at a rate of 1 out of 288 clones.

The efficiency of homologous recombination was further examined using the resulting knock-in vector. As a result, it was confirmed that positive clones could be efficiently obtained, i.e., at rates of 1 out of 60, 6 out of 180, 5 out of 175, and 2 out of 98 clones.

Example 2

Preparation of Knock-in Mouse

A gene was introduced into the ES cell of a mouse by electroporation, and the G418-resistant clones were analyzed by Southern blotting. A positive clone (ES cell), in which homologous recombination was observed, was introduced into a morula to prepare chimera mice, and the F1 mice were prepared by mating the chimera mice (germ-line preparation). A Cre enzyme-expressing plasmid was introduced into fertilized eggs that were obtained by the mating of positive F1 mice, and the unnecessary neo gene was removed. Thus, the gene substitution with a human-type gene was completed.

The resulting heterozygous human-type knock-in mice (Ki-ChM) were mated with each other to prepare homozygous mice. The resulting knock-in mice expressed a recombinant prion protein as shown in SEQ ID NO: 6 (Ki-ChM).

Similarly, knock-in mice that expressed a complete human prion protein (SEQ ID NO: 10 comprising 4 repeat sequences, which should be generally 5, of 8 amino acids,) were prepared as a control (Ki-HuM).

Example 3

Preparation of Transgenic Mice

Figure 5:
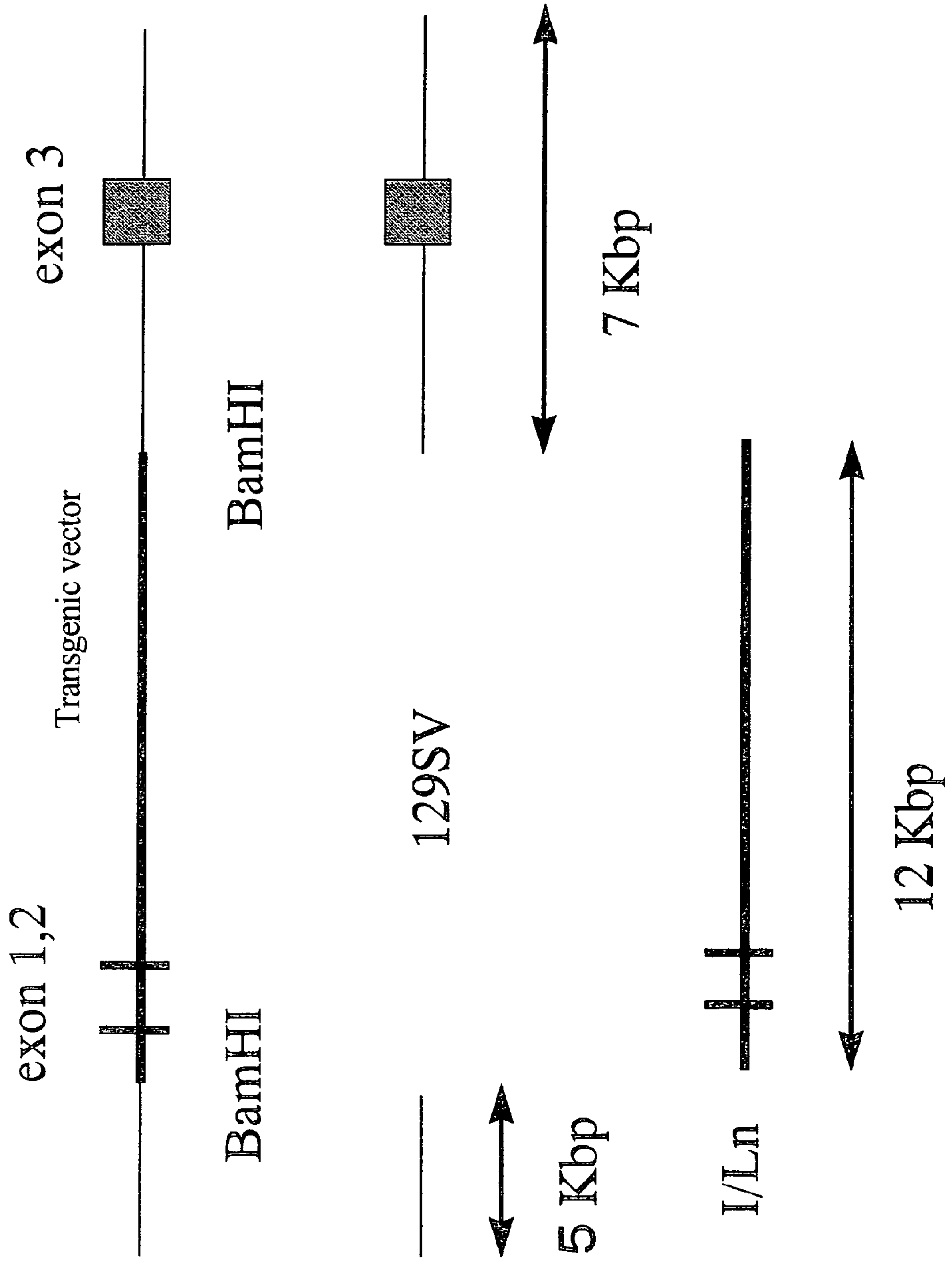
FIG. 5 shows the structure of the transgenic vector used in the present invention.

Mouse prion protein genes were cloned from two types of mice, a 129/SV mouse and an I/Ln mouse. Since the intron 2 of the 129/SV mouse is 20 kbp or longer, the gene of the I/Ln mouse with the shorter intron 2 was also used. A 5 kbp region on the 5' side of the 129/SV mouse, a 12 kbp BamHI fragment containing the exons 1 and 2 of the I/Ln mouse, and a 7 kbp exon 3 region of the 129/SV mouse were linked (FIG. 5). As with the knock-in mouse in Example 2, the region between the SmaI site and the BstEII site in the exon 3 was substituted with a human prion protein. The thus prepared transgenic vector was cleaved out of the plasmid and directly introduced into the fertilized eggs of the BDF1 mice. F0 mice, which successfully underwent the introduction, were mated to prepare F1 mice. The expression level was analyzed using this F1 mouse, the F1 mouse was mated twice with a knockout mouse. Thus, a mouse, which did not express a mouse prion protein but expressed only a recombinant prion protein (SEQ ID NO: 6 or 7) (Tg-ChM and Tg-ChV), was prepared.

Example 4

Establishment of Infection by Intracerebral Administration to Knock-in Mice and Transgenic Mice A brain emulsion was prepared from a frozen brain of a patient of human sporadic CJD in a glass homogenizer to a concentration of 10% using a phosphate buffer (PBS). The right brain hemispheres of the knock-in mice (Ki-ChM and Ki-HuM) obtained in Example 2 and three types of transgenic mice (Tg-ChM#30, Tg-ChV#21, and Tg-ChV#21) obtained in Example 3 were inoculated intracerebrally with the thus prepared brain emulsion under anesthesia using a 27-gauge syringe in amounts of 20 μl each. After the inoculation, neurological symptoms such as decreased autonomic movement, atactic gait, abnormal gait, or tail rigidity were observed and developed. Individuals that developed emaciation or debility were subjected to euthanasia and then to autopsy. It took approximately 21 days on average until the euthanasia following the development of the neurological symptom. The incubation period was the period between the day of inoculation, i.e., day 0, and the euthanasia. At the time of autopsy, mice were immobilized with buffered formalin, and some of the major organs were cryopreserved at −70° C.

All the mice were embedded in paraffin and then thinly sliced in the laboratory to prepare pathological samples of prions only. Thereafter, the mice were subjected to HE staining and immunohistostaining by the autoclave method, which we had devised, to diagnose the tissues based on the lesion and the deposition of the aberrant prion protein. Thus, the presence or absence of the prion disease was confirmed.

Regarding the Ki-ChM knock-in mice expressing a recombinant human prion protein that were inoculated with human sporadic CJD (129M/M)-H3 which was homozygous for methionine at codon 129, the incubation period was 151±6.7 days. The incubation periods in three types of transgenic mice (Tg-ChM#30, Tg-ChV#12, and Tg-ChV#21) that were inoculated with the same material were 156±14.2 days, 175±15.3 days, and 192±4.0 days, respectively (Table 1). The incubation period was significantly shortened compared to the incubation period in the Ki-HuM mice that expressed the complete human prion protein, i.e., 643±42.9 days. In contrast, Wild (wild-type) mice into which no gene was introduced had the morbidity rate of only 36%, i.e., only 5 out of 14 examples, and the incubation period therein was 759±69.8 days.

The incubation period in the knock-in mice inoculated with human sporadic CJD (129V/M)-Su which was heterozygous for valine and methionine at codon 129 was 141±5.3 days. The incubation periods in three types of transgenic mice (Tg-ChM#30, Tg-ChV#12, and Tg-Ch#21), which were similarly inoculated with heterozygous sporadic CJD (129V/M)-Ph, were 154±20.8 days, 171±9.2 days, and 188±1.4 days, respectively (Table 1).

TABLE 1

Establishment of infection by intracerebral administration of human prion

| Mouse | Materials used for inoculation | Incubation period Days ± SD | Number of individuals developed the disease/ Number of individuals inoculated | Morbidity rate (%) |
|---|---|---|---|---|
| Ki-ChM (Knock-in mouse) | Sporadic CJD (129 M/M)-H3 | 151 ± 6.7 | 7/7 | 100 |
| | Sporadic CJD (129 V/M)-Su | 141 ± 5.3 | 5/5 | 100 |
| Tg-ChM#30 (Transgenic mouse) | Sporadic CJD (129 M/M)-H3 | 156 ± 14.2 | 11/11 | 100 |
| | Sporadic CJD (129 V/M)-Ph | 154 ± 20.8 | 5/5 | 100 |
| Tg-ChV#12 (Transgenic mouse) | Sporadic CJD (129 M/M)-H3 | 175 ± 15.3 | 18/18 | 100 |
| | Sporadic CJD (129 V/M)-Ph | 171 ± 9.2 | 10/10 | 100 |
| Tg-ChV#21 (Transgenic mouse) | Sporadic CJD (129 M/M)-H3 | 192 ± 4.0 | 3/3 | 100 |
| | Sporadic CJD (129 V/M)-Ph | 188 ± 1.4 | 2/2 | 100 |
| Ki-HuM (Knock-in mouse) | Sporadic CJD (129 M/M)-H3 | 643 ± 42.9 | 4/4 | 100 |
| Wild (Wild-type mouse) | Sporadic CJD (129 M/M)-H3 | 759 ± 69.8 | 5/14* | 36 |

Mice were intracerebrally inoculated with 20 μl of 10% human brain emulsion.
*Most mice lacked clear clinical symptoms, although individuals determined to be positive by immunohistostaining were regarded as having established infection. Thus, they were classified as "developed the disease."

Accordingly, the knock-in mice and the transgenic mice that were obtained in Examples 2 and 3 according to the present invention were found to be highly susceptible to human prions, and the infectivity of human prion could be surely verified within a short period of time which had previously taken a long time and had been uncertain in conventional wild-type mice. In particular, the knock-in mice were infected within an unprecedentedly short incubation period, i.e., approximately 150 days, with a human prion that was heterozygous for methionine or valine at codon 129. This indicates that the knock-in mice according to the present invention can deal with the polymorphism of the human prion protein gene. At the same time, the incubation period for the above infection is equivalent to those among mice of mouse-adapted prions. Accordingly, it is considered that the "species barrier" in prion infection was overcome. Further, the incubation period in the knock-in mice Ki-ChM was significantly shortened compared to the long incubation period in the completely human-type knock-in mice Ki-HuM. This indicates that the vector introduced and the recombinant human prion protein expressed thereby control the susceptibility to prion of these mice.

Example 5

Histological Detection of Aberrant Prion Protein in the FDC

The FDC was examined after the knock-in mice and the transgenic mice obtained in Examples 2 and 3 had developed the disease. As a result, no aberrant prion protein was detected in the transgenic mice, although the deposition of the human-type aberrant prion protein was observed in the FDCs of the spleen, the lymph node, and the intestinal lymphoid tissue (Peyer's patch) of the knock-in mice (FIG. 2A).

Example 6

Detection of Aberrant Prion Protein by Western Blotting

We also examined the deposition of the aberrant prion protein in the spleen by Western blotting, which was already confirmed by immunostaining. The presence of the aberrant prion protein was confirmed in the spleen of the knock-in mice.

The infected spleen, an uninfected spleen (a control), and the infected brain of the knock-in mice obtained in Example 2 were analyzed by Western blotting.

When Western blotting is performed after treatment with proteinase K, it is known that three bands are formed from the aberrant prion protein. As shown in FIG. 3, the presence of the aberrant prion protein was observed in the sample derived from the infected spleen and brain since the three bands were observed. That is, a band containing no sugar chain attached from the bottom, a band containing a sugar chain attached through one site, and a band having sugar chains through two sites. In contrast, no band corresponding thereto was found in the uninfected sample. Compared to the brain, the level of the aberrant prion protein in the spleen was lower.

Example 7

Immunostaining Experiment on the FDC Using an Antibody to the C-Terminus of the Human-Type Prion Protein A monoclonal antibody to the C-terminus of the human-type prion protein was prepared. This antibody recognizes codons 215, 219, and 220 of the human prion protein (SEQ ID NO: 2), and it does not react with the amino acid sequences of the codons corresponding to those of the mouse prion protein. Codons 215, 219, and 220 of the knock-in mice obtained in Example 2 (Ki-ChM) are substituted with those of mouse-type instead of human-type. Thus, this monoclonal antibody does not react therewith, and it reacts only with a completely human-type prion protein. These knock-in mice were infected with a brain emulsion of the sporadic CJD example having a completely human-type aberrant prion protein. If the FDC simply accumulates the injected completely human-type aberrant prion protein, the FDC should be stained with this antibody. In the experiment, however, the aberrant prion protein of the knock-in mice was not stained at all. That is, it is not a simple accumulation of the injected completely human-type prion proteins, but a deposition, in the FDC, of the aberrated human-type prion protein of the knock-in mice having mouse-type C-terminuses.

Example 8

Comparison Between Transgenic Mice and Knock-in Mice

In order to examine the reason why the deposition of the aberrant prion protein was detected in the FDC of knock-in mice but not in transgenic mice in Example 5, the expression of the recombinant prion protein in the spleen was assayed by Western blotting.

Figure 6:
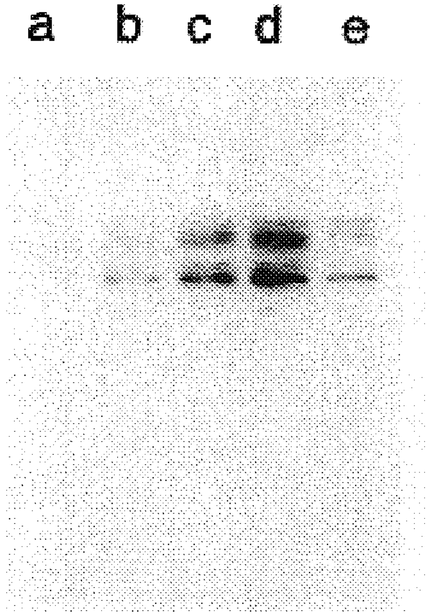
FIG. 6 shows, by Western blotting, the expression of a recombinant prion protein in the spleen of the knock-in mouse and the transgenic mouse.

The expression level of the normal prion protein in the spleen of the transgenic mouse (Tg-ChV#12), which expresses twice as many recombinant prion proteins as those expressed in the brain of the knock-in mouse (Ki-ChM), was examined by Western blotting. The results are shown in FIG. 6. In FIG. 6, “a” to “d” represent knock-in mice and “e” represents a transgenic mouse. “d” and “e” are electrophoresed fractions of the spleens of the same tissue weight, “c” is a 50% electrophoresed fraction, “b” is a 25% electrophoresed fraction, and “a” is a 12.5% electrophoresed fraction by tissue weight based on “d.” The intensity of the immune response of “e” is considered to be substantially equivalent to that of “b” and the expression level in the transgenic mice was approximately 25% of that in the knock-in mice.

This demonstrates that the distribution of expression in the transgenic mice is different from that in the wild-type mice. Specifically, the expression level in the transgenic mice is merely extremely low, and this does not mean that the recombinant prion protein is not expressed in the spleen (FDC). Accordingly, it is considered that the expression in the spleen (FDC) of the transgenic mice was determined to be negative.

Thus, the deposition of the aberrant prion protein in the FDC was found to be detectable with the use of the transgenic animals according to the present invention, if a suitable detection method was employed.

Example 9

Confirmation of Infectivity of Mice that Developed the Disease After Being Infected with Human Prion In the direct infection experiment, the infectivity of the aberrant prion proteins that were found in the brain and the spleen of the mice were verified.

The knock-in mice (Ki-ChM) obtained in Example 2 were inoculated intracerebrally with a 10% brain emulsion prepared from a sporadic CJD example. A brain emulsion was prepared from the brains and the spleens of the knock-in mice (Ki-ChM), which developed the disease, in a glass homogenizer to a concentration of 10% using a phosphate buffer (PBS). The right brain hemispheres of the knock-in mice (Ki-ChM) were inoculated intracerebrally with the brain emulsion under anesthesia using a 27-gauge syringe in amounts of 20 μl each. As with the conventional methods that were carried out in all the mouse inoculation experiments in Examples herein, neurological symptoms such as decreased autonomic movement, atactic gait, abnormal gait, or tail rigidity were observed and developed after the inoculation. Individuals that developed emaciation or debility were subjected to euthanasia and then to autopsy.

As a result, 6 out of 6 mice (100%), which were inoculated with a brain emulsion of mice that had developed the disease, developed the disease, and the incubation period was 123±10.0 days. In contrast, 5 out of 5 mice (100%), which were inoculated with a spleen emulsion of the mice that had developed the disease, developed the disease, and the incubation period was 156±7.9 days. As is apparent from these results, the presence of the infectivity as well as the deposition of the aberrant protein were confirmed in the brain and the spleen (FDC) of the knock-in mice (Ki-ChM) that had developed the diseased after the inoculation of a human brain emulsion (Table 2).

TABLE 2

Confirmation of infectivity of mice that developed the disease after being infected with human prion

| Materials used for inoculation | Inoculated mouse | Incubation period (days ± SD) | Number of individuals that developed the disease/number of individuals inoculated |
|---|---|---|---|
| Inoculation experiment 1, Human sporadic CJD, 10% brain emulsion | Ki-ChM | 151 ± 6.7 | 7/7 |

TABLE 2-continued

Confirmation of infectivity of mice that developed the disease after being infected with human prion

| Materials used for inoculation | Inoculated mouse | Incubation period (days ± SD) | Number of individuals that developed the disease/number of individuals inoculated |
|---|---|---|---|
| Inoculation experiment 2, 10% brain emulsion of mouse that developed the disease (Inoculation Experiment 1) | Ki-ChM | 123 ± 10.0 | 6/6 |
| Inoculation experiment 3, 10% spleen emulsion of mouse that developed the disease (Inoculation Experiment 1) | Ki-ChM | 156 ± 7.9 | 5/5 |

Example 10

Experiment for Detecting Aberrant Prion of CJD Patient in the FDC

A brain emulsion was prepared from the frozen brain of a CJD patient in a glass homogenizer to a concentration of 10% using a phosphate buffer (PBS). The knock-in mice (Ki-ChM) were inoculated intraperitoneally with the brain emulsion using a 26-gauze syringe in amounts of 50 μl each. Mice were subjected to euthanasia at 75 days after the inoculation and then to autopsy. At the time of autopsy, mice were immobilized with buffered formalin, and some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to examine the deposition of the aberrant prion protein in the FDC.

As a result, the aberrant prion proteins were detected in the FDCs of all the Ki-ChM mice inoculated with a human prion derived from either human sporadic CJD (129 M/M)-H3 which was homozygous for methionine at codon 129, human sporadic CJD (129 V/M)-Su which was heterozygous for valine and methionine at codon 129, or human CJD by dura mater transplantation, CJD-TMD-Du/c. Specifically, the detection rate was 100% (Table 3).

Example 11

CJD Infection by Dura Mater Transplantation

A brain emulsion was prepared from the frozen brain of a patient who was definitely diagnosed to have developed CJD after a dura mater transplantation (CJD-TMD-Du/c) in a glass homogenizer to a concentration of 10% using a phosphate buffer (PBS). The knock-in mice (Ki-ChM) were inoculated intraperitoneally with the brain emulsion using a 26-gauze syringe in amounts of 50 μl each. Mice were subjected to euthanasia at 75 days after the inoculation and then to autopsy. At the time of autopsy, mice were immobilized with buffered formalin, and some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to examine the deposition of the aberrant prion protein in the FDC.

As a result, the aberrant prion proteins were detected in the spleen FDCs of all the 5 inoculated Ki-ChM mice (Table 3).

Example 12

Detection of Aberrant Prion Derived from British nvCJD Patient

A brain emulsion was prepared from the frozen brain of a patient of new variant CJD (hereinafter abbreviated to "nvCJD"), which was presumed to have derived from BSE in Britain, in a glass homogenizer to a concentration of 10% using a phosphate buffer (PBS). In order to remove infectious agents other than prions, the brain emulsion was maintained at 60° C. for 30 minutes. Thereafter, the emulsion was cryopreserved at −70° C. until the inoculation. At the time of inoculation, the emulsion was defrosted, and the knock-in mice (Ki-ChM) were inoculated intraperitoneally therewith using a 26-gauze syringe in amounts of 50 μl each. They were subjected to euthanasia at 75 days after the inoculation and then to autopsy. At the time of autopsy, mice were immobilized with buffered formalin, and some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to examine the deposition of the aberrant prion protein in the FDC.

TABLE 3

Detection of aberrant prion of CJD patient in the FDC

| Material used for inoculation | Inoculated mice | Number of days following the inoculation | Number of positive FDC/Number of examined individuals | Detection rate |
|---|---|---|---|---|
| Sporadic CJD (129 M/M)-H3, 10% human brain emulsion | Ki-ChM | 75 | 5/5 | 100% |
| Sporadic CJD (129 V/M)-Su, 10% human brain emulsion | Ki-ChM | 75 | 5/5 | 100% |
| Dura mater transplanted CJD-TMD-Du/C, 10% human brain emulsion | Ki-ChM | 75 | 6/6 | 100% |

Mice were inoculated intraperitoneally with 50 μl of 10% human brain emulsion.

As a result, aberrant prion proteins were detected at the detection rate of 100%. Specifically, 5 out of 5, 4 out of 4, and 4 out of 4 of the three cases of nvCJD patients' brains, i.e., nv-96/02, nv-96/07, and nv-96/45, respectively.

A novel biological assay method using the FDC of the knock-in mice (Ki-ChM) according to the present invention was also useful for the diagnosis of prions derived from nvCJD patients in Britain (Table 4).

TABLE 4

| Material used for inoculation | Inoculated mice | Detection of aberrant prion of British nvCJD patient<br>Number of days from the inoculation | Number of positive FDC/Number of examined individuals | Detection rate |
|---|---|---|---|---|
| British nvCJD human 10% brain emulsion, nv-96/02 | Ki-ChM | 75 | 5/5 | 100% |
| British nvCJD human 10% brain emulsion, nv-96/07 | Ki-ChM | 75 | 4/4 | 100% |
| British nvCJD human 10% brain emulsion, nv-96/45 | Ki-ChM | 75 | 4/4 | 100% |

Mice were inoculated intraperitoneally with 50 μl of 10% human brain emulsion.

Example 13

Examination of Assay System 1 (Intracerebral and Intraperitoneal Administrations)

A brain emulsion was prepared from the frozen brain of a human CJD patient in a glass homogenizer to a concentration of 10% using a phosphate buffer (PBS). In order to remove infectious agents other than prions, the brain emulsion was maintained at 60° C. for 30 minutes. Thereafter, the emulsion was cryopreserved at −70° C. until the inoculation. At the time of inoculation, the emulsion was defrosted, and the right brain hemispheres of the knock-in mice (Ki-ChM) obtained in Example 2 were inoculated intracerebrally therewith under anesthesia using a 27-gauge syringe in amounts of 20 μl each. After the inoculation, neurological symptoms such as decreased autonomic movement, atactic gait, abnormal gait, or tail rigidity were observed and developed. Individuals that developed emaciation or debility were subjected to euthanasia and then to autopsy. It took approximately 21 days on average until the euthanasia following the development of the neurological symptom. The incubation period was the period between the day of inoculation, i.e., day 0, and the euthanasia. At the time of autopsy, mice were immobilized with buffered formalin, and some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to diagnose the tissues based on the lesion and the deposition of the aberrant prion protein. Thus, the presence or absence of the prion disease was confirmed.

TABLE 5

| Material used for inoculation | Inoculated mouse | Examination of assay system 1 (intracerebral and intraperitoneal administrations)<br>Inoculation route | Incubation period (days ± SD) | Number of individuals that developed the disease/number of individuals inoculated |
|---|---|---|---|---|
| Sporadic CJD (129M/M), human 10% brain emulsion-H3 | Ki-ChM | Intracerebral | 151 ± 6.7 | 7/7 |
| Sporadic CJD (129M/M), human 10% brain emulsion-H3 | Ki-ChM | Intraperitoneal | 283 ± 9.2 | 11/11 |
| Sporadic CJD (129V/M), human 10% brain emulsion-Su | Ki-ChM | Intracerebral | 141 ± 5.3 | 5/5 |
| Sporadic CJD (129 V/M, M232R), human 10% brain emulsion, TMD-232 | Ki-ChM | Intracerebral | 177 ± 4.9 | 4/4 |
| CJD after dura mater transplantation, human 10% brain emulsion, TMD-Du/C | Ki-ChM | Intracerebral | 167 ± 24.7 | 6/6 |

As a result, the incubation period in the knock-in nice that were inoculated with human sporadic CJD (129 M/M)-H3 which was homozygous for methionine at codon 129 was 151±6.7 days. The incubation period was extended in the case of intraperitoneal inoculation. However, all 11 mice developed the disease in 283±9.2 days. The incubation period in the knock-in mice that were inoculated with human sporadic CJD (129 V/M)-Su which was heterozygous for valine and methionine at codon 129 was 141±5.3 days. In the case of a human brain emulsion that was heterozygous and had gene mutation in which methionine at codon 232 had been substituted with arginine, the incubation period was somewhat extended, i.e., 177±4.9 days, and all the mice developed the disease. Mice, which were inoculated with a 10% brain emulsion of a human affected with CJD after dura mater transplantation, TMD-Du/C, developed the disease in the incubation period of 167±24.7 days.

Accordingly, the knock-in mice of the present invention, Ki-ChM, were found to be highly susceptible to various types of human prions. Since they are susceptible through intraperitoneal inoculation as well as intracerebral inoculation, they are presumed to be susceptible to human prion infection through various peripheries.

Example 14

Examination of Assay System 2—Observation with the Elapse of Time

A brain emulsion was prepared from a frozen brain of a human CJD patient in a glass homogenizer to a concentration of 10% using a phosphate buffer (PBS). In order to remove infectious agents other than prions, the brain emulsion was maintained at 60° C. for 30 minutes. Thereafter, the emulsion was cryopreserved at −70° C. until the inoculation. At the time of inoculation, the emulsion was defrosted, and the knock-in mice (Ki-ChM) obtained in Example 2 were then inoculated intraperitoneally therewith using a 26-gauge syringe in amounts of 50 μl each. Mice were subjected to euthanasia 14 days, 31 days, 44 days, 60 days, 75 days, or 150 days after the inoculation. At the time of autopsy, mice were immobilized with buffered formalin, and some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to detect the lesion and the aberrant prion protein.

As a result, the deposition of the aberrant prion proteins in the FDCs of 2 out of 4 knock-in mice (Ki-ChM) (50%) 14 days after the inoculation were observed by immunohistostaining. Thereafter, the aberrant prion proteins were present in the FDCs of all the inoculated mice from day 31 to day 150. Abnormal prion proteins or other histopathological changes, however, were not detected in the target organ, the central nervous system, from day 14 to day 150.

According to the FDC-based biological assay using the knock-in mice (Ki-ChM) of the present invention, aberrant prion proteins can be detected within a very short time period of 14 days. This indicates that detection can be continuously performed (Table 6).

TABLE 6

Detection of aberrant prion protein in the FDC of Ki-ChM mice with the elapse of time

| Number of days after the administration | Number of Positive FDC/number of mice examined | Detection rate |
|---|---|---|
| 14 days | 2/4 | 50% |
| 31 days | 6/6 | 100% |
| 44 days | 7/7 | 100% |
| 60 days | 6/6 | 100% |
| 75 days | 5/5 | 100% |
| 150 days | 7/7 | 100% |

Example 15

Examination of Assay System 3—Examination of Concentration

In Example 14, the deposition of the aberrant prion proteins was found to be detectable in the FDCs of the knock-in mice (Ki-ChM) according to the present invention within at least 14 days using a 10% brain emulsion of human sporadic CJD. Subsequently, the lowest detectable concentration was examined by diluting the material for inoculation.

The aforementioned 10% frozen brain emulsion (tenfold diluted) of a sporadic CJD-affected human was defrosted, and a 1% (100-fold diluted), 0.1% (1000-fold diluted,) and 0.01% (10000-fold diluted) solutions were prepared using the same PBS. The knock-in mice (Ki-ChM) that were obtained in Example 2 were inoculated intraperitoneally with the brain emulsion using a 26-gauze syringe in amounts of 50 μl each. Mice were subjected to euthanasia at 75 days after the inoculation and then immobilized on buffered formalin. All the samples were embedded in paraffin and then thinly sliced in the laboratory to prepare pathological samples of prions only. Thereafter, they were subjected to immunohistostaining by the autoclave method, which we had devised, to detect the deposition of the aberrant prion protein.

As a result, aberrant prion proteins were detected in the FDCs of 80% or more individuals inoculated with a 0.01% (10,000-fold diluted) solution.

This indicates that the use of the FDC of the knock-in mice (Ki-ChM) of the present invention enables the detection of infectivity of sporadic CJD-infected human brain even if it is diluted 10,000-fold or more.

Example 16

Comparison of Susceptibility Between Knock-in Mice Ki-ChM and Ki-HuM

Susceptibility to prion by intracerebral inoculation and that by intraperitoneal inoculation were compared using two types of knock-in mice, Ki-ChM and Ki-Hun, which were obtained in Example 2. Specifically, the right brain hemisphere of the knock-in mice (Ki-ChM and Ki-HuM) obtained in Example 2 were inoculated intracerebrally with a 10% brain emulsion of the sporadic CJD (129 M/M)-H3 example using a 27-gauge syringe in amounts of 20 μl each. Also, 50 μl each of the brain emulsion was injected intraperitoneally using a 26-gauze syringe.

In the case of intracerebral inoculation, neurological symptoms such as decreased autonomic movement, atactic gait, abnormal gait, or tail rigidity were observed and developed after the inoculation, as with the conventional methods that were carried out in all the mouse inoculation experiments in Examples herein. Individuals that developed emaciation or debility were subjected to euthanasia and then to autopsy. The incubation period was the period between the day of inoculation, i.e., day 0, and the euthanasia. At the time of autopsy, mice were immobilized with buffered formalin, and some of the major organs were cryopreserved at −70° C.

In the case of intraperitoneal inoculation, mice were subjected to euthanasia 75 days after the inoculation and then to autopsy. At the time of autopsy, they were immobilized with buffered formalin. Some of the major organs were cryopreserved at −70° C. All the mice were embedded in paraffin and then thinly sliced in the laboratory to prepare pathological samples of prions only. Thereafter, the mice were subjected to HE staining and immunohistostaining by the autoclave method, which we had devised, to detect the deposition of the aberrant prion protein in the FDC.

Consequently, all the human-type knock-in mice Ki-ChM developed the disease within the incubation period of 151±6.7 days. Although all the knock-in mice (Ki-HuM) that expressed complete human prion proteins (SEQ ID NO: 10 comprising 4 repeat sequences, which should be generally 5, of 8 amino acids) developed the disease, it required a very long incubation period of 643±42.9 days. According to immunohistostaining of the spleen FDC 75 days after the intraperitoneal inoculation, aberrant prion proteins were detected at 100% (5 out of 5 mice) in the case of Ki-ChM. The detection rate, however, was just 80% (4 out of 5 mice) in the case of Ki-HuM (Table 7).

TABLE 7

Comparison of susceptibility between knock-in mice Ki-ChM and Ki-HuM

| | | Lineage of mice | |
|---|---|---|---|
| Inoculation route | | Ki-ChM | Ki-HuM |
| Intracerebral inoculation | Incubation period | 151 ± 6.7 | 643 ± 42.9 |
| | Number of crisis | 7/7 (100%) | 4/4 (100%) |
| Intraperitoneal inoculation | Positive FDC (75 days later) | 5/5 (100%) | 4/5 (100%) |

All mice were inoculated with 10% brain emulsion of sporadic CJD (129 M/M)-H3.

In consideration of both the incubation period in the case of intracerebral inoculation and the detection rate of aberrant prion proteins in the FDC 75 days later, aberrant prion proteins were found to be always deposited in the FDCs of the knock-in mice regardless of their constructs. Specifically, the use of the knock-in method, wherein the prion proteins are effectively expressed in the FDC, enables effective observation of aberration in the FDC to some extent in the case of completely human-type animals, wherein aberration of prion protein is unlikely to occur in brains. At the same time, even in a lineage having a long incubation period, i.e., a completely human-type animal in which aberration is unlikely to occur in the brain, the probability of aberrant prion protein deposition in the FDC does not reach 100%. This means that the deposition of the aberrant prion protein in the FDC reflects the susceptibility of mice to human prions. Also, it reflects the fact that the aberration of completely human-type prion proteins is highly unlikely to occur.

INDUSTRIAL APPLICABILITY

As described above, the present invention enabled the preparation of an animal model that is unprecedentedly highly susceptible to human prion proteins. With the use of this animal model, the present invention can provide a novel screening method that can be used in safety tests of human or non-human animal prion diseases.

The knock-in animal that is obtained by the present invention is excellent for use in an assay system for nvCJD aberrant prion proteins. In particular, in the case of intraperitoneal administration, the amount of infectious agents used for inoculation can be raised to 100 times compared with that of intracerebral administration. The infectivity of blood, which is considered to be low, can be investigated by administering a large amount thereof.

Accordingly, the knock-in animal of the present invention will be essential for final safety tests of preparations that are produced from blood or organs of human or non-human animals.

nvCJD is considered to infect as follows. The aberrant prion protein is first deposited in the tonsilla and the FDC of lymphoid tissues of digestive organs by ingesting bovine prion proteins. The aberrant prion protein is then transported from the FDC to the brain. As with the case of this nvCJD, the knock-in animal obtained by the present invention was found to develop the disease through the deposition of the aberrant prion protein in the FDC through peripheral routes, followed by transportation of the aberrant prion protein to the brain. This was verified through their infection with human prions. Accordingly, this model can be effective not only in the establishment of rapid biological assay but also in a screening system for developing medicines to block the aberrant prion proteins from being transported from the FDC to the brain in the future.

All publications, patents, and patent applications cited herein are incorporated herein by reference in their entirety.

The invention claimed is:

1. A process of diagnosing the presence of infectious agents of human prion diseases in a sample, comprising a) obtaining a knock-in rodent that expresses a humanized prion protein, wherein the humanized prion protein is prepared by substituting the region between the SmaI site and the BstEII site in exon 3 of the non-human animal prion gene with the region between the SmaI site and the BstEII site in exon 3 of the human prion gene;

b) administering to the rodent a sample suspected of containing infectious agents of human prion diseases; and c) from 14 to about 75 days after the administration, detecting deposition of an aberrant prion protein in follicular dendritic cell (FDC) of the rodent, wherein the deposition indicates the presence of the infectious agent in the sample.

2. A process of diagnosing the presence of infectious agents of human prion diseases in a sample, comprising a) obtaining a knock-in rodent that expresses a humanized prion protein, wherein the humanized prion protein is prepared by substituting human specific amino acid residues 193, 197, 198, 205, 206 and 208 of SEQ ID NO: 3 with corresponding amino acid residues in the rodent prion protein;

b) administering to the rodent a sample suspected of containing infectious agents of human prion protein diseases; and c) from 14 to about 75 days after the administration, detecting deposition of an aberrant prion protein in follicular dendritic cell (FDC) of the rodent, wherein the deposition indicates the presence of the infectious agent in the sample.

3. A process of diagnosing the presence of infectious agents of human prion diseases in a sample, comprising a) obtaining a knock-in rodent that expresses a humanized prion protein, wherein the humanized prion protein comprises amino acid sequence as shown in SEQ ID NO: 6 or 7;

b) administering to the rodent a sample suspected of containing infectious agents of human prion diseases; and c) from 14 to about 75 days after the administration, detecting deposition of an aberrant prion protein in follicular dendritic cell (FDC) of the rodent, wherein the deposition indicates the presence of the infectious agent in the sample.

4. The process of diagnosis according to claim 1, wherein the sample is administered intraperitoneally, intracerebrally, intravascularly, or orally to the rodent.

5. The process of diagnosis according to claim 2, wherein the sample is administered intraperitoneally, intracerebrally, intravascularly, or orally to the rodent.

* * * * *

SEQUENCE LISTING

```
<160> NUMBER OF SEQ ID NOS: 10

<210> SEQ ID NO 1
<211> LENGTH: 762
<212> TYPE: DNA
<213> ORGANISM: Homo sapiens
<220> FEATURE:
<221> NAME/KEY: CDS
<222> LOCATION: (1)..(762)

<400> SEQUENCE: 1
```

-continued

```
atg gcg aac ctt ggc tgc tgg atg ctg gtt ctc ttt gtg gcc aca tgg        48
Met Ala Asn Leu Gly Cys Trp Met Leu Val Leu Phe Val Ala Thr Trp
  1               5                  10                  15

agt gac ctg ggc ctc tgc aag aag cgc ccg aag cct gga gga tgg aac        96
Ser Asp Leu Gly Leu Cys Lys Lys Arg Pro Lys Pro Gly Gly Trp Asn
             20                  25                  30

act ggg ggc agc cga tac ccg ggg cag ggc agc cct gga ggc aac cgc       144
Thr Gly Gly Ser Arg Tyr Pro Gly Gln Gly Ser Pro Gly Gly Asn Arg
         35                  40                  45

tac cca cct cag ggc ggt ggt ggc tgg ggg cag cct cat ggt ggt ggc       192
Tyr Pro Pro Gln Gly Gly Gly Gly Trp Gly Gln Pro His Gly Gly Gly
     50                  55                  60

tgg ggg cag cct cat ggt ggt ggc tgg ggg cag ccc cat ggt ggt ggc       240
Trp Gly Gln Pro His Gly Gly Gly Trp Gly Gln Pro His Gly Gly Gly
 65                  70                  75                  80

tgg gga cag cct cat ggt ggt ggc tgg ggt caa gga ggt ggc acc cac       288
Trp Gly Gln Pro His Gly Gly Gly Trp Gly Gln Gly Gly Gly Thr His
                 85                  90                  95

agt cag tgg aac aag ccg agt aag cca aaa acc aac atg aag cac atg       336
Ser Gln Trp Asn Lys Pro Ser Lys Pro Lys Thr Asn Met Lys His Met
            100                 105                 110

gct ggt gct gca gca gct ggg gca gtg gtg ggg ggc ctt ggc ggc tac       384
Ala Gly Ala Ala Ala Ala Gly Ala Val Val Gly Gly Leu Gly Gly Tyr
        115                 120                 125

atg ctg gga agt gcc atg agc agg ccc atc ata cat ttc ggc agt gac       432
Met Leu Gly Ser Ala Met Ser Arg Pro Ile Ile His Phe Gly Ser Asp
    130                 135                 140

tat gag gac cgt tac tat cgt gaa aac atg cac cgt tac ccc aac caa       480
Tyr Glu Asp Arg Tyr Tyr Arg Glu Asn Met His Arg Tyr Pro Asn Gln
145                 150                 155                 160

gtg tac tac agg ccc atg gat gag tac agc aac cag aac aac ttt gtg       528
Val Tyr Tyr Arg Pro Met Asp Glu Tyr Ser Asn Gln Asn Asn Phe Val
                165                 170                 175

cac gac tgc gtc aat atc aca atc aag cag cac acg gtc acc aca acc       576
His Asp Cys Val Asn Ile Thr Ile Lys Gln His Thr Val Thr Thr Thr
            180                 185                 190

acc aag ggg gag aac ttc acc gag acc gac gtt aag atg atg gag cgc       624
Thr Lys Gly Glu Asn Phe Thr Glu Thr Asp Val Lys Met Met Glu Arg
        195                 200                 205

gtg gtt gag cag atg tgt atc acc cag tac gag agg gaa tct cag gcc       672
Val Val Glu Gln Met Cys Ile Thr Gln Tyr Glu Arg Glu Ser Gln Ala
    210                 215                 220

tat tac cag aga gga tcg agc atg gtc ctc ttc tcc tct cca cct gtg       720
Tyr Tyr Gln Arg Gly Ser Ser Met Val Leu Phe Ser Ser Pro Pro Val
225                 230                 235                 240

atc ctc ctg atc tct ttc ctc atc ttc ctg ata gtg gga tga               762
Ile Leu Leu Ile Ser Phe Leu Ile Phe Leu Ile Val Gly
                245                 250


<210> SEQ ID NO 2
<211> LENGTH: 253
<212> TYPE: PRT
<213> ORGANISM: Homo sapiens

<400> SEQUENCE: 2

Met Ala Asn Leu Gly Cys Trp Met Leu Val Leu Phe Val Ala Thr Trp
  1               5                  10                  15

Ser Asp Leu Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
```

-continued

```
        35                  40                  45

Tyr Pro Pro Gln Gly Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250


<210> SEQ ID NO 3
<211> LENGTH: 208
<212> TYPE: PRT
<213> ORGANISM: Homo sapiens

<400> SEQUENCE: 3

Lys Lys Arg Pro Lys Pro Gly Gly Trp Asn Thr Gly Gly Ser Arg Tyr
  1               5                  10                  15

Pro Gly Gln Gly Ser Pro Gly Gly Asn Arg Tyr Pro Pro Gln Gly Gly
             20                  25                  30

Gly Gly Trp Gly Gln Pro His Gly Gly Gly Trp Gly Gln Pro His Gly
        35                  40                  45

Gly Gly Trp Gly Gln Pro His Gly Gly Gly Trp Gly Gln Pro His Gly
    50                  55                  60

Gly Gly Trp Gly Gln Gly Gly Gly Thr His Ser Gln Trp Asn Lys Pro
65                  70                  75                  80

Ser Lys Pro Lys Thr Asn Met Lys His Met Ala Gly Ala Ala Ala Ala
                85                  90                  95

Gly Ala Val Val Gly Gly Leu Gly Gly Tyr Met Leu Gly Ser Ala Met
            100                 105                 110

Ser Arg Pro Ile Ile His Phe Gly Ser Asp Tyr Glu Asp Arg Tyr Tyr
        115                 120                 125

Arg Glu Asn Met His Arg Tyr Pro Asn Gln Val Tyr Tyr Arg Pro Met
    130                 135                 140

Asp Glu Tyr Ser Asn Gln Asn Asn Phe Val His Asp Cys Val Asn Ile
145                 150                 155                 160
```

-continued

```
Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
            180                 185                 190

Ile Thr Gln Tyr Glu Arg Glu Ser Gln Ala Tyr Tyr Gln Arg Gly Ser
        195                 200                 205


<210> SEQ ID NO 4
<211> LENGTH: 768
<212> TYPE: DNA
<213> ORGANISM: Artificial Sequence
<220> FEATURE:
<223> OTHER INFORMATION: Description of Artificial Sequence:
                         Chimera-type prion gene
<220> FEATURE:
<221> NAME/KEY: CDS
<222> LOCATION: (1)..(768)

<400> SEQUENCE: 4

atg gcg aac ctt ggc tac tgg ctg ctg gcc ctc ttt gtg act atg tgg       48
Met Ala Asn Leu Gly Tyr Trp Leu Leu Ala Leu Phe Val Thr Met Trp
  1               5                  10                  15

act gat gtc ggc ctc tgc aaa aag cgg cca aag cct gga ggg tgg aac       96
Thr Asp Val Gly Leu Cys Lys Lys Arg Pro Lys Pro Gly Gly Trp Asn
             20                  25                  30

acc ggt gga agc cgg tat ccc ggg cag ggc agc cct gga ggc aac cgc      144
Thr Gly Gly Ser Arg Tyr Pro Gly Gln Gly Ser Pro Gly Gly Asn Arg
         35                  40                  45

tac cca cct cag ggc ggt ggt ggc tgg ggg cag cct cat ggt ggt ggc      192
Tyr Pro Pro Gln Gly Gly Gly Gly Trp Gly Gln Pro His Gly Gly Gly
     50                  55                  60

tgg ggg cag cct cat ggt ggt ggc tgg ggg cag ccc cat ggt ggt ggc      240
Trp Gly Gln Pro His Gly Gly Gly Trp Gly Gln Pro His Gly Gly Gly
 65                  70                  75                  80

tgg gga cag cct cat ggt ggt ggc tgg ggt caa gga ggt ggc acc cac      288
Trp Gly Gln Pro His Gly Gly Gly Trp Gly Gln Gly Gly Gly Thr His
                 85                  90                  95

agt cag tgg aac aag ccg agt aag cca aaa acc aac atg aag cac atg      336
Ser Gln Trp Asn Lys Pro Ser Lys Pro Lys Thr Asn Met Lys His Met
            100                 105                 110

gct ggt gct gca gca gct ggg gca gtg gtg ggg ggc ctt ggc ggc tac      384
Ala Gly Ala Ala Ala Ala Gly Ala Val Val Gly Gly Leu Gly Gly Tyr
        115                 120                 125

rtg ctg gga agt gcc atg agc agg ccc atc ata cat ttc ggc agt gac      432
Xaa Leu Gly Ser Ala Met Ser Arg Pro Ile Ile His Phe Gly Ser Asp
    130                 135                 140

tat gag gac cgt tac tat cgt gaa aac atg cac cgt tac ccc aac caa      480
Tyr Glu Asp Arg Tyr Tyr Arg Glu Asn Met His Arg Tyr Pro Asn Gln
145                 150                 155                 160

gtg tac tac agg ccc atg gat gag tac agc aac cag aac aac ttt gtg      528
Val Tyr Tyr Arg Pro Met Asp Glu Tyr Ser Asn Gln Asn Asn Phe Val
                165                 170                 175

cac gac tgc gtc aat atc aca atc aag cag cac acg gtc acc acc acc      576
His Asp Cys Val Asn Ile Thr Ile Lys Gln His Thr Val Thr Thr Thr
            180                 185                 190

acc aag ggg gag aac ttc acc gag acc gat gtg aag atg atg gag cgc      624
Thr Lys Gly Glu Asn Phe Thr Glu Thr Asp Val Lys Met Met Glu Arg
        195                 200                 205

gtg gtg gag cag atg tgc gtc acc cag tac cag aag gag tcc cag gcc      672
Val Val Glu Gln Met Cys Val Thr Gln Tyr Gln Lys Glu Ser Gln Ala
    210                 215                 220
```

-continued

```
tat tac gac ggg aga aga tcc agc agc acc gtg ctt ttc tcc tcc cct      720
Tyr Tyr Asp Gly Arg Arg Ser Ser Ser Thr Val Leu Phe Ser Ser Pro
225                 230                 235                 240

cct gtc atc ctc ctc atc tcc ttc ctc atc ttc ctg atc gtg gga tga      768
Pro Val Ile Leu Leu Ile Ser Phe Leu Ile Phe Leu Ile Val Gly
                245                 250                 255


<210> SEQ ID NO 5
<211> LENGTH: 255
<212> TYPE: PRT
<213> ORGANISM: Artificial Sequence
<220> FEATURE:
<223> OTHER INFORMATION: Description of Artificial Sequence:
                         Chimera-type prion protein
<220> FEATURE:
<221> NAME/KEY: VARIANT
<222> LOCATION: 129
<223> OTHER INFORMATION: Xaa=Met or Val

<400> SEQUENCE: 5

Met Ala Asn Leu Gly Tyr Trp Leu Leu Ala Leu Phe Val Thr Met Trp
  1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Gly Gly Trp Gly Gln Pro His Gly Gly Gly
     50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Ser Gln Trp Asn Lys Pro Ser Lys Pro Lys Thr Asn Met Lys His Met
             100                 105                 110

Ala Gly Ala Ala Ala Ala Gly Ala Val Val Gly Gly Leu Gly Gly Tyr
         115                 120                 125

Xaa Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
             180                 185                 190

Thr Lys Gly Glu Asn Phe Thr Glu Thr Asp Val Lys Met Met Glu Arg
         195                 200                 205

Val Val Glu Gln Met Cys Val Thr Gln Tyr Gln Lys Glu Ser Gln Ala
    210                 215                 220

Tyr Tyr Asp Gly Arg Arg Ser Ser Ser Thr Val Leu Phe Ser Ser Pro
225                 230                 235                 240

Pro Val Ile Leu Leu Ile Ser Phe Leu Ile Phe Leu Ile Val Gly
                245                 250                 255


<210> SEQ ID NO 6
<211> LENGTH: 209
<212> TYPE: PRT
<213> ORGANISM: Artificial Sequence
<220> FEATURE:
<223> OTHER INFORMATION: Description of Artificial Sequence:
                         ChM-type prion protein
```

-continued

<400> SEQUENCE: 6

```
Lys Lys Arg Pro Lys Pro Gly Gly Trp Asn Thr Gly Gly Ser Arg Tyr
  1               5                  10                  15

Pro Gly Gln Gly Ser Pro Gly Gly Asn Arg Tyr Pro Pro Gln Gly Gly
             20                  25                  30

Gly Gly Trp Gly Gln Pro His Gly Gly Gly Trp Gly Gln Pro His Gly
         35                  40                  45

Gly Gly Trp Gly Gln Pro His Gly Gly Gly Trp Gly Gln Pro His Gly
     50                  55                  60

Gly Gly Trp Gly Gln Gly Gly Gly Thr His Ser Gln Trp Asn Lys Pro
 65                  70                  75                  80

Ser Lys Pro Lys Thr Asn Met Lys His Met Ala Gly Ala Ala Ala Ala
                 85                  90                  95

Gly Ala Val Val Gly Gly Leu Gly Gly Tyr Met Leu Gly Ser Ala Met
            100                 105                 110

Ser Arg Pro Ile Ile His Phe Gly Ser Asp Tyr Glu Asp Arg Tyr Tyr
        115                 120                 125

Arg Glu Asn Met His Arg Tyr Pro Asn Gln Val Tyr Tyr Arg Pro Met
    130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
            180                 185                 190

Val Thr Gln Tyr Gln Lys Glu Ser Gln Ala Tyr Tyr Asp Gly Arg Arg
        195                 200                 205

Ser
```

<210> SEQ ID NO 7
<211> LENGTH: 209
<212> TYPE: PRT
<213> ORGANISM: Artificial Sequence
<220> FEATURE:
<223> OTHER INFORMATION: Description of Artificial Sequence:
ChV type prion protein

<400> SEQUENCE: 7

```
Lys Lys Arg Pro Lys Pro Gly Gly Trp Asn Thr Gly Gly Ser Arg Tyr
  1               5                  10                  15

Pro Gly Gln Gly Ser Pro Gly Gly Asn Arg Tyr Pro Pro Gln Gly Gly
             20                  25                  30

Gly Gly Trp Gly Gln Pro His Gly Gly Gly Trp Gly Gln Pro His Gly
         35                  40                  45

Gly Gly Trp Gly Gln Pro His Gly Gly Gly Trp Gly Gln Pro His Gly
     50                  55                  60

Gly Gly Trp Gly Gln Gly Gly Gly Thr His Ser Gln Trp Asn Lys Pro
 65                  70                  75                  80

Ser Lys Pro Lys Thr Asn Met Lys His Met Ala Gly Ala Ala Ala Ala
                 85                  90                  95

Gly Ala Val Val Gly Gly Leu Gly Gly Tyr Val Leu Gly Ser Ala Met
            100                 105                 110

Ser Arg Pro Ile Ile His Phe Gly Ser Asp Tyr Glu Asp Arg Tyr Tyr
        115                 120                 125
```

-continued

```
Arg Glu Asn Met His Arg Tyr Pro Asn Gln Val Tyr Tyr Arg Pro Met
    130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
            180                 185                 190

Val Thr Gln Tyr Gln Lys Glu Ser Gln Ala Tyr Tyr Asp Gly Arg Arg
        195                 200                 205

Ser


<210> SEQ ID NO 8
<211> LENGTH: 765
<212> TYPE: DNA
<213> ORGANISM: Mus musculus
<220> FEATURE:
<221> NAME/KEY: CDS
<222> LOCATION: (1)..(765)

<400> SEQUENCE: 8

atg gcg aac ctt ggc tac tgg ctg ctg gcc ctc ttt gtg act atg tgg       48
Met Ala Asn Leu Gly Tyr Trp Leu Leu Ala Leu Phe Val Thr Met Trp
  1               5                  10                  15

act gat gtc ggc ctc tgc aaa aag cgg cca aag cct gga ggg tgg aac       96
Thr Asp Val Gly Leu Cys Lys Lys Arg Pro Lys Pro Gly Gly Trp Asn
             20                  25                  30

acc ggt gga agc cgg tat ccc ggg cag gga agc cct gga ggc aac cgt      144
Thr Gly Gly Ser Arg Tyr Pro Gly Gln Gly Ser Pro Gly Gly Asn Arg
         35                  40                  45

tac cca cct cag ggt ggc acc tgg ggg cag ccc cac ggt ggt ggc tgg      192
Tyr Pro Pro Gln Gly Gly Thr Trp Gly Gln Pro His Gly Gly Gly Trp
     50                  55                  60

gga caa ccc cat ggg ggc agc tgg gga caa cct cat ggt ggt agt tgg      240
Gly Gln Pro His Gly Gly Ser Trp Gly Gln Pro His Gly Gly Ser Trp
 65                  70                  75                  80

ggt cag ccc cat ggc ggt gga tgg ggc caa gga ggg ggt acc cat aat      288
Gly Gln Pro His Gly Gly Gly Trp Gly Gln Gly Gly Gly Thr His Asn
                 85                  90                  95

cag tgg aac aag ccc agc aaa cca aaa acc aac ctc aag cat gtg gca      336
Gln Trp Asn Lys Pro Ser Lys Pro Lys Thr Asn Leu Lys His Val Ala
            100                 105                 110

ggg gct gcg gca gct ggg gca gta gtg ggg ggc ctt ggt ggc tac atg      384
Gly Ala Ala Ala Ala Gly Ala Val Val Gly Gly Leu Gly Gly Tyr Met
        115                 120                 125

ctg ggg agc gcc gtg agc agg ccc atg atc cat ttt ggc aac gac tgg      432
Leu Gly Ser Ala Val Ser Arg Pro Met Ile His Phe Gly Asn Asp Trp
    130                 135                 140

gag gac cgc tac tac cgt gaa aac atg tac cgc tac cct aac caa gtg      480
Glu Asp Arg Tyr Tyr Arg Glu Asn Met Tyr Arg Tyr Pro Asn Gln Val
145                 150                 155                 160

tac tac agg cca gtg gat cag tac agc aac cag aac aac ttc gtg cac      528
Tyr Tyr Arg Pro Val Asp Gln Tyr Ser Asn Gln Asn Asn Phe Val His
                165                 170                 175

gac tgc gtc aat atc acc atc aag cag cac acg gtc acc acc acc acc      576
Asp Cys Val Asn Ile Thr Ile Lys Gln His Thr Val Thr Thr Thr Thr
            180                 185                 190

aag ggg gag aac ttc acc gag acc gat gtg aag atg atg gag cgc gtg      624
Lys Gly Glu Asn Phe Thr Glu Thr Asp Val Lys Met Met Glu Arg Val
        195                 200                 205
```

-continued

```
gtg gag cag atg tgc gtc acc cag tac cag aag gag tcc cag gcc tat      672
Val Glu Gln Met Cys Val Thr Gln Tyr Gln Lys Glu Ser Gln Ala Tyr
    210                 215                 220

tac gac ggg aga aga tcc agc agc acc gtg ctt ttc tcc tcc cct cct      720
Tyr Asp Gly Arg Arg Ser Ser Ser Thr Val Leu Phe Ser Ser Pro Pro
225                 230                 235                 240

gtc atc ctc ctc atc tcc ttc ctc atc ttc ctg atc gtg gga tga          765
Val Ile Leu Leu Ile Ser Phe Leu Ile Phe Leu Ile Val Gly
                245                 250                 255


<210> SEQ ID NO 9
<211> LENGTH: 254
<212> TYPE: PRT
<213> ORGANISM: Mus musculus

<400> SEQUENCE: 9

Met Ala Asn Leu Gly Tyr Trp Leu Leu Ala Leu Phe Val Thr Met Trp
  1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly Trp
     50                  55                  60

Gly Gln Pro His Gly Gly Ser Trp Gly Gln Pro His Gly Gly Ser Trp
 65                  70                  75                  80

Gly Gln Pro His Gly Gly Gly Trp Gly Gln Gly Gly Gly Thr His Asn
                 85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Val Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250


<210> SEQ ID NO 10
<211> LENGTH: 200
<212> TYPE: PRT
<213> ORGANISM: Homo sapiens

<400> SEQUENCE: 10

Lys Lys Arg Pro Lys Pro Gly Gly Trp Asn Thr Gly Gly Ser Arg Tyr
  1               5                  10                  15
```

-continued

```
Pro Gly Gln Gly Ser Pro Gly Gly Asn Arg Tyr Pro Pro Gln Gly Gly
                20                  25                  30

Gly Gly Trp Gly Gln Pro His Gly Gly Gly Trp Gly Gln Pro His Gly
            35                  40                  45

Gly Gly Trp Gly Gln Pro His Gly Gly Gly Trp Gly Gln Gly Gly Gly
        50                  55                  60

Thr His Ser Gln Trp Asn Lys Pro Ser Lys Pro Lys Thr Asn Met Lys
 65                  70                  75                  80

His Met Ala Gly Ala Ala Ala Ala Gly Ala Val Val Gly Gly Leu Gly
                 85                  90                  95

Gly Tyr Met Leu Gly Ser Ala Met Ser Arg Pro Ile Ile His Phe Gly
            100                 105                 110

Ser Asp Tyr Glu Asp Arg Tyr Tyr Arg Glu Asn Met His Arg Tyr Pro
        115                 120                 125

Asn Gln Val Tyr Tyr Arg Pro Met Asp Glu Tyr Ser Asn Gln Asn Asn
    130                 135                 140

Phe Val His Asp Cys Val Asn Ile Thr Ile Lys Gln His Thr Val Thr
145                 150                 155                 160

Thr Thr Thr Lys Gly Glu Asn Phe Thr Glu Thr Asp Val Lys Met Met
                165                 170                 175

Glu Arg Val Val Glu Gln Met Cys Ile Thr Gln Tyr Glu Arg Glu Ser
            180                 185                 190

Gln Ala Tyr Tyr Gln Arg Gly Ser
        195                 200
```